US010555994B2

(12) United States Patent
Hernandez et al.

(10) Patent No.: US 10,555,994 B2
(45) Date of Patent: Feb. 11, 2020

(54) PCV2 ORF2 CARRIER PLATFORM

(71) Applicant: Boehringer Ingelheim Animal Health USA Inc., Duluth, GA (US)

(72) Inventors: Luis Alejandro Hernandez, Story City, IA (US); Eric Martin Vaughn, Ames, IA (US)

(*) Notice: Subject to any disclaimer, the term of this patent is extended or adjusted under 35 U.S.C. 154(b) by 0 days.

(21) Appl. No.: 15/562,167

(22) PCT Filed: Mar. 29, 2016

(86) PCT No.: PCT/US2016/024631
§ 371 (c)(1),
(2) Date: Sep. 27, 2017

(87) PCT Pub. No.: WO2016/160761
PCT Pub. Date: Oct. 6, 2016

(65) Prior Publication Data
US 2018/0344835 A1    Dec. 6, 2018

Related U.S. Application Data

(60) Provisional application No. 62/140,284, filed on Mar. 30, 2015.

(51) Int. Cl.
| | | |
|---|---|---|
| *A61K 39/12* | (2006.01) |
| *C07K 14/005* | (2006.01) |
| *C12N 15/62* | (2006.01) |
| *C07K 1/14* | (2006.01) |
| *G01N 33/53* | (2006.01) |
| *G01N 33/566* | (2006.01) |
| *A61P 31/20* | (2006.01) |
| *A61K 39/00* | (2006.01) |

(52) U.S. Cl.
CPC .............. *A61K 39/12* (2013.01); *A61P 31/20* (2018.01); *C07K 1/14* (2013.01); *C07K 14/005* (2013.01); *C12N 15/62* (2013.01); *G01N 33/5308* (2013.01); *G01N 33/566* (2013.01); *A61K 2039/5258* (2013.01); *A61K 2039/552* (2013.01); *A61K 2039/6075* (2013.01); *C07K 2319/40* (2013.01); *C12N 2750/10022* (2013.01); *C12N 2750/10023* (2013.01); *C12N 2750/10034* (2013.01); *C12N 2770/10022* (2013.01); *C12N 2770/10034* (2013.01); *C12N 2799/026* (2013.01)

(58) Field of Classification Search
None
See application file for complete search history.

(56) References Cited

U.S. PATENT DOCUMENTS 9,505,808 B2 * 11/2016 Hernandez ........... C07K 14/005
10,131,696 B2 * 11/2018 Hernandez ........... C07K 14/005
2009/0017064 A1 * 1/2009 Wu .................. A61K 39/12
424/205.1
2011/0280905 A1 * 11/2011 Meng ................ C12N 7/00
424/204.1
2018/0344835 A1 * 12/2018 Hernandez ............ A61K 39/12

FOREIGN PATENT DOCUMENTS

| CN | 104693310 A | 6/2015 |
| WO | 2012005732 A1 | 1/2012 |
| WO | 2015051099 A1 | 4/2015 |
| WO | 2016160761 A2 | 10/2016 |

OTHER PUBLICATIONS

Guo et al. (Virology Journal. 2010; 7: 273).*
Alignment of SEQ ID No. 1 with UniProt db access No. A7YF28_PCV2 by Guo et al 2010.*
Alignment of SEQ ID No. 2 with UniProt db access No. A7YF28_PCV2 by Guo et al 2010.*
Huang et al. (BMC Microbiology. 2011; 11: 188).*
Beach et al., "Chimeric Porcine Circoviruses (PVC) Containing Amino Acid Epitope Tags in the C Terminus of the Capsid Gene Are Infectious and Elicit both Anti-Epitope Tag Antibodies and Anti-PCV Type 2 Neutralizing Antibodies in Pigs". Journal of Virology, vol. 85, No. 9, May 2011, pp. 4591-4595.
Database WPI, Week 201562, AN 2015-38559T, Thomson Scientific, London, GB; Jun. 10, 2015, 2 pagees.
Guo et al., "Porcine circovirus type 2 (PCV2): genetic variation and newly emerging gentoypes in China." Virology Journal, vol. 7, No. 1, , 2010, pp. 1-12 (273).
"Generation and immunogenicity of porcine circovirus type 2 chimeric virus-like particles displaying porcine reproductive and respiratory syndrome virus GP5 epitope B." Vaccine, vol. 34, No. 16, 2016, pp. 1896-1903.
International Search Report and Written Opinion for PCT/US2016/024631 dated Oct. 24, 2016.
Kekarainen et al., "Genetic variability of porcine circovirus 2 in vaccinating and non-vaccinating commercial farms." Journal of General Virology, vol. 95, 2014, pp. 1734-1742.

(Continued)

*Primary Examiner* — Shanon A. Foley
(74) *Attorney, Agent, or Firm* — Judy Jaracki-Black

(57) ABSTRACT

The present invention relates to an immunogen-carrier, wherein the immunogen-carrier is preferably a virus-like particle (VLP) composed of a plurality of a modified PCV2 ORF2 protein. In particular, the present invention belongs to the field of compliance markers and marker vaccines which allow for the differentiation between infected and vaccinated individuals. In particular, it relates to a compliance marker for vaccines including a subunit antigen, and a DIVA (Differentiating Infected from Vaccinated Animals) system which makes it possible to differentiate between animals infected with a pathogen and animals treated with a subunit antigen derived from said pathogen.

49 Claims, 4 Drawing Sheets
Specification includes a Sequence Listing.

(56) References Cited

OTHER PUBLICATIONS

Khayat et al., "The 2.3-Angstrom Structure of Porcine Circovirus 2." Journal of Virology, vol. 85, No. 15, Aug. 2011, pp. 7856-7862.
Trible et al., "Antibody Recognition of Porcine Circovirus Type 2 Capsid Protein Epitopes after Vaccination, Infection, and Disease." Clinical and Vaccine Immunology, vol. 18, No. 5, May 2011, pp. 749-757.
Trible et al., "Genetic variation of porcine circovirus type 2 (PCV2) and its relevance to vaccination, pathogenesis and diagnosis." Virus Research, vol. 164, 2012, pp. 68-77.

* cited by examiner

A.

B.

A.

B.

PCV2 ORF2 CARRIER PLATFORM

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Technical Field

The present invention relates to an immunogen-carrier, wherein the immunogen-carrier is preferably a virus-like particle (VLP) composed of a plurality of a modified PCV2 ORF2 protein. In particular, the present invention belongs to the field of compliance markers and marker vaccines which allow for the differentiation between infected and vaccinated individuals. In particular, it relates to a compliance marker for vaccines including a subunit antigen, and a DIVA (Differentiating Infected from Vaccinated Animals) system which makes it possible to differentiate between animals infected with a pathogen and animals treated with a subunit antigen derived from said pathogen.

Background Information

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV-1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all signs will be apparent while other swine will only have one or two of these clinical signs. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia.

Currently, there are three subtypes of PCV2 known (PCV2a, PCV2b and PCV2c), which are classified according to a unified nomenclature for PCV2 genotypes (Segales, J. et al., 2008, PCV-2 genotype definition and nomenclature, Vet Rec 162:867-8). Two further subtypes (PCV2d and PCV2e) have been proposed (Wang et al., Virus Res. 2009 145(1): 151-6) but, however, it was demonstrated later that they belong to the PCV2a and PCV2b clusters (Cortey et al., Vet Microbiol. 2011 149(3-4):522-32011). According to this unified nomenclature for PCV2 genotypes the orf2 gene is used to perform genotyping for pcv-2, wherein the genotyping is based on the proportion of nucleotide sites at which two sequences being compared are different (p distance). This value is obtained by dividing the number of nucleotide differences by the total number of nucleotides compared (Kumar et al., 2001 Bioinformatics 17, 1244-1245) and subsequently, the construction of a p distance/frequency histogram enables to determine potential cut-off values to distinguish different genotypes (Rogers and Harpending, 1992 Molecular Biology and Evolution 9, 552-569; Biagini et al., 1999 Journal of General Virology 80, 419-424). Using this methodology, ORF2 PCV-2 sequences are assigned to different genotypes when the genetic distance between them is 0-035.

WO2011116094 A2 discloses a chimeric porcine circovirus infectious DNA clone and live attenuated chimeric virus with the PCV2 of subtype PCV2b, and a capsid gene of subtype PCV2b integrated into a non-pathogenic PCV1 virus genome, wherein the attenuated chimeric virus can be used as a live vaccine, as well as an inactivated (killed) vaccine.

Vaccination is an essential tool to manage herd health, in particular in high density confinement settings where many food animals are raised. When disease outbreaks occur in animals that were supposedly vaccinated, questions arise as to whether the vaccine failed to protect the animals or whether the vaccine was delivered properly, wherein the latter possibility regarding proper delivery of the vaccine is referred to as vaccine compliance.

The use of compliance markers for determining if an animal has been properly vaccinated is thus highly desired by producers. WO 2009/058835 A1 describes e.g. the use of purified xylanase which was added as a compliance marker to a swine influenza vaccine.

Vaccines used in programs for controlling viral outbreaks and infections must have an effective system to monitor for continued presence of viral infection within the population. However, vaccination complicates large scale surveillance for the spread of the infection by e.g. serological means, as both vaccinated and exposed individuals produce antibody specific for the virus. The antigenic similarity between the infecting virulent field strain of the virus and the viral vaccine frequently hampers the discrimination between infected and vaccinated subjects as vaccination results in the occurrence and persistence of antibodies that are indistinguishable between infected and vaccinated individuals.

There is increasing worldwide interest in DIVA (differentiating infected and vaccinated animals) vaccination strategies. For example, the joint WHO/FAO/OIE meetings on avian influenza strain H5N1 HPAI have recommended that all vaccination is practiced using a DIVA, so spread of infection can be monitored. However, current DIVA methods are difficult to scale-up and often have problems with the differentiation of vaccination from infection with other circulating viral strains.

Current methods of monitoring include physical tagging of vaccinated animals, the use of sentinel animals, and virological testing. However, these current methods have a number of limitations due to logistical and economic reasons.

The physical tagging of vaccinated animals involves the time consuming individual identification of vaccinated individuals by physical means such as ear tags, leg bands or wing tags. Also, the use of unvaccinated sentinel animals is logistically and economically difficult and there is also a risk that if sentinels become infected with the virus, e.g. poultry infected with H5N1 virus, there is increased risk of spread to humans. Virological testing of individuals via screening and detection of live virus or RT-PCR surveillance testing is a very expensive and infrastructure heavy process, which is not applicable for subunit vaccines, and only provides information relating to the current status of an individual, and does not allow analysis of the infection and/or vaccination history of that individual.

In view of said limitations, the use of marker vaccines allowing a serological discrimination of vaccinated and infected animals is highly preferable, wherein such marker vaccines can be prepared either as negative or positive marker vaccine.

A negative marker vaccine is prepared by using an antigenic portion of the pathogen or by the removal of an antigen from the pathogen, which provokes specific antibodies in infected animals. Negative marker vaccines are usually either subunit vaccines or attenuated live vaccines containing a genetically engineered strain lacking an immunogenic antigen. An example for a negative marker vaccine is e.g., the use of baculovirus-expressed classical swine fever virus (CSFV) E2 protein as a subunit antigen for vaccinating against classical swine fever, wherein a detection of antibodies specific for other antigens of CSFV, e.g., $E^{RNS}$ protein or NS3 protein, in sera of vaccinated pigs shows a CSFV infection.

A positive marker vaccine contains an additional antigen which induces specific antibodies in vaccinated individuals but not in infected ones. An example for a positive marker vaccine approach is described in WO 2007/053899 A1, where inactivated H6N2 Avian Influenza (AI) virus and tetanus toxin, both of which separately produced, were combined in one injection for vaccinating birds, and subsequently antibodies specific for tetanus toxin were detected in sera obtained from said birds as markers showing that the birds were vaccinated.

However, the separate production of both the vaccine antigen and the marker antigen is relatively expensive.

In view of the above, a simple carrier system is needed useful as platform for inexpensively producing positive marker vaccines and effective compliance markers and, additionally, allowing a strong immunization of animals against PCV2 and, as the case may be, at least one further pathogen.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein FIG. 1. PCV2b ORF2-c-myc bands were detected in stained protein gels by size comparison to PCV2b ORF2. Lane 1, Baculo/PCV2b ORF2 c-myc pellet; Lane 2: Purified PCV2b ORF2 VLPS; Lane 3: Baculo/pVL1393 No Insert Control. A. Comassie blue stained western blot; B. anti-PCV2B Swine poly-clonal antibody stained western blot; C. anti-c-myc monoclonal antibody 9E10 stained western blot, D. anti-c-myc monoclonal antibody 9E101 stained western blot; E. anti-c-myc polyclonal rabbit antibody stained western blot; PCV2b ORF2-c-myc was detected by both anti-PCV2b antibody and anti-c-myc antibody while PCV2b ORF2 antigen was detected only by PCV2b antibody.

DESCRIPTION OF THE INVENTION

Figure 1:
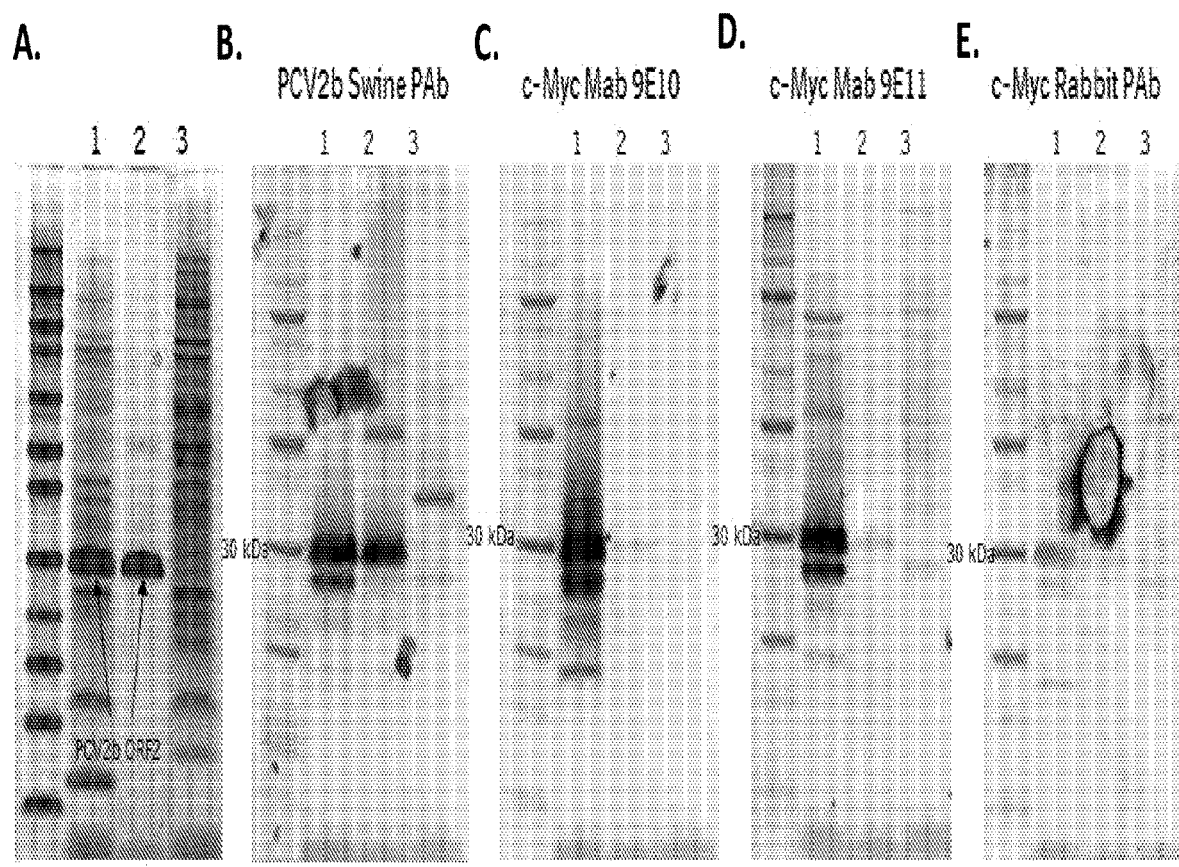

The solution to the above technical problems is achieved by the description and the embodiments characterized in the claims.

Thus, the invention in its different aspects is implemented according to the claims.

The invention is based on the surprising finding that replacing amino acid residues in the BC loop of PCV2 ORF2 protein by an epitope of interest allows for the production of VLPs presenting the epitope of interest and thereby triggering an immune response against said epitope, while retaining their antigenic properties in terms of providing active acquired immunity against PCV2.

In a first aspect the invention thus relates to a polypeptide, being is also termed "the polypeptide of the present invention" hereinafter, which is selected from the group consisting of the following (a), (b), and (c):
   a. a PCV2 ORF2 protein characterized in that at least one amino acid residue in the BC loop is replaced by an amino acid sequence of interest;
   b. a PCV2 ORF2 protein characterized in that an amino acid sequence of interest is inserted into the BC loop;
   c. a combination of (a) and (b).

The BC loop, as described herein, is in particular understood to be the region of the amino acid positions 58 to 66, wherein the numbering of the amino acid positions refers to the amino acid sequence of wild type PCV2 ORF2 protein.

It is further understood that the term "replacing amino acid residues of the BC loop" is in particular equivalent to the term "replacing amino acid residues in the BC loop".

As described herein, the numbering of amino acid positions refers to the amino acid sequence of full length wild type PCV2 ORF2 protein (SEQ ID NO:2 or SEQ ID NO:3). Hence, the numbering of the amino positions as mentioned herein is with reference to a wild type PCV2 ORF2 protein sequence having 234 or 233 amino acid residues, including a methionine residue at the (N-terminal) amino acid position 1.

Preferably, the amino acid sequence of interest is an amino acid sequence comprising or consisting of at least two or three amino acid residues or preferably of at least eight amino acid residues.

The amino acid sequence of interest preferably comprises or consists of a heterologous amino acid sequence. As used herein the term "heterologous amino acid sequence" refers to any amino acid sequence other than a PCV2 ORF2 sequence. More particularly, the term "heterologous amino acid sequence" refers to an amino acid sequence not found in that virus, e.g., the proteins of PCV2.

Preferably, the amino acid sequence of interest is selected from the group consisting of an epitope of interest, a biological response modulator, a growth factor, a recognition sequence, a fusion protein.

Preferably, the amino acid sequence of interest comprises or consists of an epitope of interest, and wherein the epitope of interest is preferably an amino acid sequence comprising or consisting of 8 to 25 amino acid residues.

The epitope of interest is preferably an epitope of interest from an antigen or a veterinary pathogen or toxin, and wherein the epitope of interest is more preferably a peptide comprising the c-myc tag peptide or a peptide encoded by the orf5 gene of PRRS virus.

The peptide encoded by the orf5 gene of PRRS virus preferably comprises or consists of the amino acid sequence of SEQ ID NO:6 or preferably comprises or consists of at least 8 consecutive amino acid residues of the sequence set forth in SEQ ID NO: 6.

Preferably, the polypeptide of the invention according to aspect (a) is a PCV2 ORF2 protein characterized in that at least one amino acid residue in the region of the amino acid positions 58 to 64 is replaced by an amino acid sequence of interest, and wherein the numbering of the amino acid positions refers to the amino acid sequence of wild type PCV2 ORF2 protein.

The polypeptide of the invention according to aspect (a) is preferably a PCV2 ORF2 protein characterized in that at least two or three amino acid residues in the BC loop are replaced by an amino acid sequence of interest, and wherein preferably two, three, four, five, six, or seven amino acid residues in the BC loop are replaced by an amino acid sequence of interest.

Preferably, the polypeptide according to aspect (a) is a polypeptide of the invention, wherein:

- the six amino acid residues of the amino acid positions 58 to 63 are replaced by an amino acid sequence of interest, wherein the numbering of the amino acid positions refers to the amino acid sequence of wild type PCV2 ORF2 protein; and/or
- the amino acid of interest comprises or consists of an amino acid sequence consisting of 11 amino acid residues, and/or
- the amino acid of interest comprises or consists of the sequence of SEQ ID NO:5 or SEQ ID NO:7.

The polypeptide of the present invention is preferably a recombinant protein, more preferably a recombinant baculovirus expressed protein.

The term "recombinant protein", as used herein, in particular refers to a protein molecule which is expressed from a recombinant DNA molecule, such as a polypeptide which is produced by recombinant DNA techniques. An example of such techniques includes the case when DNA encoding the expressed protein is inserted into a suitable expression vector, preferably a baculovirus expression vector, which is in turn used to transfect, or in case of a baculovirus expression vector to infect, a host cell to produce the protein or polypeptide encoded by the DNA. The term "recombinant protein", as used herein, thus in particular refers to a protein molecule which is expressed from a recombinant DNA molecule.

According to a particular example, the recombinant protein is produced by a method with the following steps: The gene for polypeptide of the present invention is cloned into a baculovirus transfer vector; the transfer vector is used to prepare recombinant baculovirus containing said gene by homologous recombination in insect cells; and the protein is then expressed in insect cells during infection with the recombinant baculovirus.

According to an alternative example, the recombinant protein is expressed in insect cells from a recombinant expression plasmid. In the case of this alternative example baculovirus is not needed.

It is further understood that the term "recombinant protein comprising or consisting of a sequence" in particular also concerns any cotranslational and/or posttranslational modification or modifications of the sequence affected by the cell in which the polypeptide is expressed. Thus, the term "recombinant protein comprising or consisting of a sequence", as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

Preferably, the recombinant protein according to the invention is produced or obtainable by a baculovirus expression system, in particular in cultured insect cells.

Preferably, the polypeptide of the present invention is a. a PCV2 ORF2 protein characterized in that at least one amino acid residue in the BC loop is replaced by an amino acid sequence of interest;
b. a PCV2 ORF2 protein characterized in that an amino acid sequence of interest is inserted into the BC loop;
c. a combination of (a) and (b), wherein said PCV2 ORF2 protein is a PCV2 subtype b (PCV2b) ORF2 protein or a PCV2 subtype a (PCV2a) ORF2 protein and/or wherein said PCV2 ORF2 protein comprises or consists of an amino acid sequence having at least 90% sequence identity with the amino acid sequence of SEQ ID NO:2 or SEQ ID NO:3.

The polypeptide of the present invention preferably comprises or consists of an amino acid sequence having at least 90%, preferably at least 92%, more preferably at least 94%, even more preferably at least 96%, still more preferably at least 98%, or in particular 100% sequence identity with the amino acid sequence of SEQ ID NO:1.

In still another preferred aspect of the present invention, the wild type PCV2 ORF2 protein, as described herein, is the protein set forth in SEQ ID NO:2 or SEQ ID NO:3.

According to another aspect, the invention further provides an immunogenic composition containing the polypeptide of the present invention.

According to another preferred aspect, the invention further provides an immunogenic composition containing the polypeptide of the present invention, and a PCV2a ORF2 polypeptide, wherein said PCV2a ORF2 polypeptide is preferably a polypeptide that is at least 94% or preferably at least 95% identical to the sequence of SEQ ID NO: 3.

According to a further aspect, the invention also provides a polynucleotide comprising a sequence which encodes the polypeptide of the present invention, wherein said polynucleotide according to the invention is preferably an isolated polynucleotide.

For explanatory purposes and in a non-limiting example, the polynucleotide according to the invention is a polynucleotide comprising the sequence set forth in SEQ ID NO: 4.

Production of the polynucleotides described herein is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, N.Y.; Amusable, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

Also, the invention in particular provides a baculovirus which contains a polynucleotide comprising a sequence which encodes the polypeptide of the present invention, wherein said baculovirus according to the invention is preferably an isolated baculovirus.

Further, the invention also provides a plasmid, preferably an expression vector, which comprises a polynucleotide comprising a sequence which encodes the polypeptide of the present invention, wherein said plasmid according to the invention is in particular an isolated plasmid.

The invention also provides a cell comprising a baculovirus which contains a polynucleotide comprising a sequence which encodes the polypeptide of the present invention, or a plasmid, preferably an expression vector, which comprises a polynucleotide comprising a sequence which encodes the polypeptide of the present invention, wherein said cell according to the invention is preferably an isolated cell.

In still another aspect, the invention also relates to the use of the polypeptide of the present invention; the baculovirus according to the invention; the immunogenic composition according to the invention; the polynucleotide according to the invention; the plasmid according to the invention; and/or the cell according to the invention for the preparation of a medicament, preferably of a vaccine.

In this context, the invention also provides a method of producing the polypeptide of the present invention of, wherein said method comprises the step of infecting a cell, preferably an insect cell, with the baculovirus of the invention.

Further, the invention also provides a method of producing the polypeptide of the present invention, wherein said method comprises the step of transfecting a cell with the plasmid according to the invention.

The polypeptide of the present invention is preferably expressed in high amounts sufficient for the stable self-assembly of virus like particles (VLPs), which may then be used for a single shot vaccination, in particular if they are contained in an immunogenic composition, thereby allowing the reduction and prevention of clinical signs caused by an infection with PCV2, such as an infection with PCV2b and/or PCV2a.

The invention is thus in particular further based on the polypeptide of the present invention or on the immunogenic composition according to the invention, respectively, wherein said polypeptide of the present invention or said immunogenic composition comprising the polypeptide of the present invention may be used for particular purposes.

In one aspect, the invention thus relates to the polypeptide of the present invention or an immunogenic composition comprising the polypeptide of the present invention for use in a method for the treatment or prevention of an infection with PCV2, the reduction, prevention or treatment of clinical signs caused by an infection with PCV2, or the prevention or treatment of a disease caused by an infection with PCV2.

The invention also provides a method for the treatment or prevention of an infection with PCV2, the reduction, prevention or treatment of clinical signs caused by an infection with PCV2, or the prevention or treatment of a disease caused by an infection with PCV2, comprising administering the polypeptide of the present invention or an immunogenic composition comprising the polypeptide of the present invention to an animal, in particular to an animal in need thereof.

Also, the invention provides the use of the polypeptide of the present invention or of an immunogenic composition comprising the polypeptide of the present invention for the preparation of a medicament for the treatment or prevention of an infection with PCV2, the reduction, prevention or treatment of clinical signs caused by an infection with PCV2, or the treatment or prevention of a disease caused by an infection with PCV2.

In a preferred aspect, the infection with PCV2, as described herein, is an infection with PCV2 subtype b (PCV2b) and/or an infection with PCV2 of a subtype other than subtype 2b.

As used herein, the term "infection with PCV2" is equivalent to the term "PCV2 infection".

In particular, the infection with PCV2 of a subtype other than subtype 2b, as mentioned herein, is an infection with PCV2 subtype a (PCV2a) and/or PCV2 subtype c (PCV2c), and is preferably an infection with PCV2a.

The term "PCV2 subtype b (PCV2b) ORF2 protein", as described herein, relates to the protein encoded by the ORF2 gene of a PCV-2b as defined by the standardized nomenclature for PCV2 genotype definition (Segales, J. et al., 2008, PCV-2 genotype definition and nomenclature, Vet Rec 162:867-8) which is incorporated herein by reference).

According to another preferred aspect, the infection with PCV2 of a subtype other than subtype 2b, as described herein, is a concurrent infection with (i) PCV2 of a subtype other than subtype 2b and (ii) PCV2b, in particular a concurrent infection with PCV2a and PCV2b.

The terms "PCV2a", "PCV2b" and "PCV2c", respectively, as described herein, relate to PCV-2a, PCV-2b and PCV-2c, respectively, according to the standardized nomenclature for PCV2 genotype definition (Segales, J. et al., 2008, PCV-2 genotype definition and nomenclature, Vet Rec 162:867-8, which is incorporated herein by reference).

In particular, the infection with PCV2b, as mentioned herein, is an infection with (i) a PCV2 comprising a polypeptide that is at least 94%, preferably at least 95%, more preferably at least 96%, still more preferably at least 97%, yet more preferably at least 98%, and most preferably at least 99% identical to the sequence of SEQ ID NO: 2, or (ii) a PCV2 comprising a polynucleotide which comprises a sequence encoding a polypeptide that is at least 94%, preferably at least 95%, more preferably at least 96%, still more preferably at least 97%, yet more preferably at least 98%, and most preferably at least 99% identical to the sequence of SEQ ID NO:2.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. Likewise, as used herein, it is in particular understood that the term "sequence identity with the amino acid sequence of SEQ ID NO: X" is equivalent to the term "sequence identity with the amino acid sequence of SEQ ID NO:X over the length of SEQ ID NO: X" or to the term "sequence identity with the amino acid sequence of SEQ ID NO:X over the whole length of SEQ ID NO: X", respectively.

In this context, "X" is any integer selected from 1 to 3 so that "SEQ ID NO: X" represents any of the SEQ ID NOs mentioned herein in the context of sequence identity.

Preferably, the infection with PCV2a, as described herein, is an infection with (i) a PCV2 comprising a polypeptide that is at least 94%, preferably at least 95%, more preferably at least 96%, still more preferably at least 97%, yet more preferably at least 98%, and most preferably at least 99% identical to the sequence of SEQ ID NO:3, or (ii) a PCV2 comprising a polynucleotide which comprises a sequence encoding a polypeptide that is at least 94%, preferably at least 95%, more preferably at least 96%, still more preferably at least 97%, yet more preferably at least 98%, and most preferably at least 99% identical to the sequence of SEQ ID NO:3.

Preferably, in the context of the present invention, the treatment or prevention of an infection with PCV2 is based on or comprises or consists of the induction of an immune response against said PCV2, the clinical signs, as mentioned herein, are selected from the group consisting of lymphoid depletion, lymphoid inflammation, positive IHC for PCV2 antigen of lymphoid tissue, viremia, nasal shedding, pyrexia, reduced average daily weight gain, lung inflammation, positive IHC for PCV2 antigen of lung tissue, and/or the disease, as mentioned herein, PMWS.

In particular, in the context of the present invention, the treatment or prevention of an infection with PCV2 of a subtype other than 2b is based on or comprises or consists of the induction of an immune response against said PCV2 of a subtype other than 2b or the concurrent induction of an immune response against said PCV2 of a subtype other than 2b and PCV2b.

The term "prevention" or "reduction" or "preventing" or "reducing", respectively, as used herein, means, but is not limited to a process which includes the administration of a PCV2 antigen, namely of the polypeptide of the present invention, which is included in the composition of the invention, to an animal, wherein said PCV2 antigen, when administered to said animal elicits or is able to elicit an immune response in said animal against PCV2. Altogether, such treatment results in reduction of the clinical signs of a disease caused by PCV2 or of clinical signs associated with PCV2 infection, respectively. More specifically, the term "prevention" or "preventing", as used herein, means generally a process of prophylaxis in which an animal is exposed to the immunogenic composition of the present invention prior to the induction or onset of the disease process caused by PCV2.

Herein, "reduction of clinical signs associated with PCV2 infection" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of pathogen load, pathogen shedding, reduction in pathogen transmission, or reduction of any clinical sign symptomatic of PCV2 infection. Preferably these clinical signs are reduced in subjects receiving the composition of the present invention by at least 10% in comparison to subjects not receiving the composition and may become infected. More preferably, clinical signs are reduced in subjects receiving the composition of the present invention by at least 20%, preferably by at least 30%, more preferably by at least 40%, and even more preferably by at least 50%.

The term "reduction of viremia" means, but is not limited to, the reduction of PCV2 virus entering the bloodstream of an animal, wherein the viremia level, i.e., the number of PCV2 RNA copies per mL of blood serum or the number of plaque forming colonies per deciliter of blood serum, is reduced in the blood serum of subjects receiving the composition of the present invention by at least 50% in comparison to subjects not receiving the composition and may become infected. More preferably, the viremia level is reduced in subjects receiving the composition of the present invention by at least 90%, preferably by at least 99.9%, more preferably by at least 99.99%, and even more preferably by at least 99.999%.

As used herein, the term "viremia" is particularly understood as a condition in which PCV2 particles reproduce and circulate in the bloodstream of an animal.

The term "animal" or "individual", as used herein, in particular relates to a mammal, preferably to swine, more preferably to a pig, most preferably to a piglet.

According to a particular preferred aspect of the invention, the polypeptide of the present invention or the immunogenic composition according to the invention is administered only once.

Preferably, in the context of the present invention, the polypeptide of the present invention or the immunogenic composition according to the invention is to be administered or is administered, respectively, in particular only once, to an animal, preferably to a swine, more preferably to a pig, in particular preferably to a piglet.

The present invention overcomes the problems inherent in the prior art and provides a distinct advance in the state of the art. According to another aspect, the present invention also provides a method for the treatment or prevention of a PCV2 infection or for reduction of clinical signs caused by or associated with a PCV2 infection in animals, preferably animals having anti-PCV2 antibodies, comprising the step of administering an effective amount of the polypeptide of the present invention or the immunogenic composition according to the invention to that animal in need of such treatment.

The terms "vaccine" or "immunogenic composition" (both terms are used synonymously) as used herein refers to any pharmaceutical composition containing the polypeptide of the present invention, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2 mutant.

It is in particular understood that the term "PCV2 mutant", as described herein, relates to a PCV2 mutant comprising the polypeptide of the present invention and/or the polynucleotide according to the invention.

According to another aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering an effective amount of the polypeptide of the present invention or an immunogenic composition comprising the polypeptide of the present invention to that animal in need of such treatment, wherein the immunogenic composition is subunit immunogenic composition, a composition containing whole killed, or attenuated and/or inactivated PCV2.

The term "subunit immunogenic composition" as used herein refers to a composition containing at least one immunogenic polypeptide or antigen, but not all antigens, derived from or homologous to an antigen from a PCV2 mutant. Such a composition is substantially free of intact PCV2 mutant. Thus, a "subunit immunogenic composition" is prepared from at least partially purified or fractionated (preferably substantially purified) immunogenic polypeptides from a PCV2 mutant, or recombinant analogs thereof. A subunit immunogenic composition can comprise the subunit antigen or antigens of interest substantially free of other antigens or polypeptides from a PCV2 mutant, or in fractionated from. A preferred immunogenic subunit composition comprises the polypeptide of the present invention as described herein.

An "immune response" means but is not limited to the development in a host of a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the signs associated with PCV2 infections, in particular an infection with PCV2 subtype b (PCV2b) and/or an infection with PCV2 of a subtype other than subtype 2b, in delay of onset of viremia, in a reduced viral persistence, in a reduction of the overall viral load and/or a reduction of viral excretion.

The term "antigen" as used herein refers to an amino acid sequence which elicits an immunological response as described above.

According to a further aspect, the immunogenic composition as used herein most preferably comprises the polypeptide of the present invention, or a fragment thereof, expressed by the polypeptide according to the invention. A preferred polypeptide of the present invention is that of SEQ ID NO: 1. However, it is understood by those of skill in the art that this sequence could vary by as much as 1-5% in sequence homology and still retain the antigenic characteristics that render it useful in immunogenic compositions according to invention.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1): 387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, according to a further aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering an effective amount of the polypeptide of the present invention or an immunogenic composition comprising the polypeptide of the present invention to that animal in need of such treatment, wherein said the polypeptide of the present invention is anyone of those, described herein. Preferably, the polypeptide of the present invention protein is: (i) a polypeptide comprising or consisting of the sequence of SEQ ID NO: 1; or (ii) any polypeptide that is at least 95% homologous to the polypeptide of (i).

According to a further aspect, the polypeptide of the present invention is provided in the immunogenic composition at a protein inclusion level effective for inducing the desired immune response, namely reducing the incidence of, lessening the severity of, or preventing or reducing one or more clinical signs resulting from or associated with a PCV2 infection. Preferably, the inclusion level of the polypeptide of the present invention is at least 0.2 μg protein/ml of the final immunogenic composition (μg/ml), more preferably from about 0.2 to about 400 μg/ml, still more preferably from about 0.3 to about 200 μg/ml, even more preferably from about 0.35 to about 100 μg/ml, still more preferably from about 0.4 to about 50 μg/ml, still more preferably from about 0.45 to about 30 μg/ml, still more preferably from about 0.5 to about 18 μg/ml, even more preferably from about 0.6 to about 15 μg/ml even more preferably from about 0.75 to about 8 μg/ml, even more preferably from about 1.0 to about 6 μg/ml, still more preferably from about 1.3 to about 3.0 μg/ml, even more preferably from about 1.4 to about 2.5 μg/ml, even more preferably from about 1.5 to about 2.0 μg/ml, and most preferably about 1.6 μg/ml.

According to a further aspect, the protein inclusion level is at least 0.2 μg/PCV2b ORF-2 protein as described above per dose of the final immunogenic composition (jig/dose), more preferably from about 0.2 to about 400 μg/dose, still more preferably from about 0.3 to about 200 μg/dose, even more preferably from about 0.35 to about 100 μg/dose, still more preferably from about 0.4 to about 50 μg/dose, still more preferably from about 0.45 to about 30 μg/dose, still more preferably from about 0.5 to about 18 μg/dose, even more preferably from about 0.6 to about 15 μg/ml, even more preferably from about 0.75 to about 8 μg/dose, even more preferably from about 1.0 to about 6 μg/dose, still more preferably from about 1.3 to about 3.0 μg/dose, even more preferably from about 1.4 to about 2.5 μg/dose, even more preferably from about 1.5 to about 2.0 μg/dose, and most preferably about 1.6 μg/dose. Also, an inclusion level of the polypeptide of the present invention (antigen content) of less than 20 μg/dose, preferably of about 0.5 to 18 μg/dose is suitable to confer immunity in young animals and/or in animals which are positive for PCV2 antibodies, in particular which are positive for anti-PCV2 maternal derived antibodies. Thus, according to a further aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering less than 20 μg/dose, preferably of about 0.5 to 18 μg/dose of the polypeptide of the present invention or an immunogenic composition comprising the polypeptide of the present invention to that animal in need of such treatment. Said polypeptide of the present invention is anything described in this patent application.

The polypeptide of the present invention used in the immunogenic composition in accordance with the present invention can be derived in any fashion including isolation and purification of the polypeptide of the present invention, standard protein synthesis, and recombinant methodology. Preferred methods for obtaining the polypeptide of the present invention are provided in WO06/072065, the teachings and content of which are hereby incorporated by reference in its entirety, since surprisingly it has been found that the methods described therein for obtaining PCV2a ORF-2 polypeptide can be used accordingly for obtaining the polypeptide of the present invention. Briefly, susceptible cells are infected with a recombinant viral vector containing DNA coding sequences encoding the polypeptide of the present invention, the polypeptide of the present invention protein is expressed by the recombinant virus, and the expressed polypeptide of the present invention is recovered from the supernatant by filtration and inactivated by any conventional method, preferably using binary ethylenimine (BEI), which is then neutralized to stop the inactivation process.

The immunogenic composition as used herein also refers to a composition that comprises i) any of the polypeptides of the present invention described above, preferably in concentrations described above, and ii) at least a portion of the viral vector expressing said polypeptide of the present invention, preferably of a recombinant baculovirus. Moreover, the immunogenic composition may comprise i) any of the polypeptides of the present invention described above, preferably in concentrations described above, ii) at least a portion of the viral vector expressing said polypeptide of the present invention, preferably of a recombinant baculovirus, and iii) a portion of the cell culture supernatant.

Thus, according to a further aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering an effective amount of the polypeptide of the present invention or an immunogenic composition comprising the polypeptide of the present invention to that animal in need of such treatment, wherein the polypeptide of the present invention is a recombinant, preferably a baculovirus expressed, polypeptide of the present invention. Preferably those recombinant or baculovirus expressed polypeptides of the present invention have the sequence as described above.

The immunogenic composition as used herein also refers to a composition that comprises i) any of the polypeptides of the present invention described above, preferably in concentrations described above, ii) at least a portion of the viral vector expressing said polypeptide of the present invention, preferably of a recombinant baculovirus, and iii) a portion of the cell culture; wherein about 90% of the components have a size smaller than 1 µm.

The immunogenic composition as used herein also refers to a composition that comprises i) any of the polypeptides of the present invention described above, preferably in concentrations described above, ii) at least a portion of the viral vector expressing said polypeptide of the present invention, iii) a portion of the cell culture, iv) and inactivating agent to inactivate the recombinant viral vector, preferably BEI, wherein about 90% of the components i) to iii) have a size smaller than 1 µm. Preferably, BEI is present in concentrations effective to inactivate the baculovirus, preferably in an amount of 2 to about 8 mM BEI, preferably of about 5 mM BEI.

The immunogenic composition as used herein also refers to a composition that comprises i) any of the polypeptides of the present invention described above, preferably in concentrations described above, ii) at least a portion of the viral vector expressing said polypeptide of the present invention, iii) a portion of the cell culture, iv) an inactivating agent to inactivate the recombinant viral vector, preferably BEI, and v) a neutralization agent to stop the inactivation mediated by the inactivating agent, wherein about 90% of the components i) to iii) have a size smaller than 1 µm. Preferably, if the inactivating agent is BEI, said composition comprises sodium thiosulfate in equivalent amounts to BEI.

The protein is incorporated into a composition that can be administered to an animal susceptible to PCV2 infection. In preferred forms, the composition may also include additional components known to those of skill in the art (see also, Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises the polypeptide of the present invention as provided herewith, preferably in concentrations described above, which is mixed with an adjuvant, preferably CARBOPOL® (The Lubrizol Corporation), and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g., saline or corresponding plasma protein solutions are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g., anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular PLURONIC® products, especially L121 (BASF Corp.). See Hunter et al., The Theory and Practical Application of Adjuvants (Ed. Stewart-Tull, D. E. S.). John Wiley and Sons, NY, pp 51-94 (1995) and Todd et al, Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g., vinyls, allyls and other ethylenically unsaturated groups. The unsaturated radicals may themselves contain other substituents, such as methyl. The products sold under the name CARBOPOL® (The Lubrizol Corporation) are particularly appropriate. They are cross-linked with an allyl sucrose or with allyl pentaerythritol. Among them, there may be mentioned CARBOPOL® 974P, 934P and 97 IP. Most preferred is the use of CARBOPOL®, in particular the use of CARBOPOL® 971P, preferably in amounts of about 500 μg to about 5 mg per dose, even more preferred in an amount of about 750 μg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 μg to about 5 mg per dose. Even more preferably, the adjuvant is added in an amount of about 750 μg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains polypeptide of the present invention recovered from the supernatant of in vitro cultured cells, wherein said cells were infected with a recombinant viral vector containing DNA encoding the polypeptide of the present invention and expressing the polypeptide of the present invention, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

The present invention also relates to an immunogenic composition that comprises i) any of the polypeptides of the present invention described above, preferably in concentrations described above, ii) at least a portion of the viral vector expressing said polypeptide of the present invention, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BET; and vi) a suitable adjuvant, preferably CARBOPOL® 971 in amounts described above; wherein about 90% of the components i) to iii) have a size smaller than 1 μm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml (i) at least 1.6 μg of the polypeptide of the present invention described above, preferably less than 20 μg (ii) at least a portion of baculovirus expressing said polypeptide of the present invention (iii) a portion of the cell culture, (iv) about 2 to 8 mM BEI, (v) sodium thiosulfate in equivalent amounts to BEI; and (vi) about 1 mg CARBOPOL® 971, and (vii) phosphate salt in a physiologically acceptable concentration; wherein about 90% of the components (i) to (iii) have a size smaller than 1 μm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention may readily be determined by the skilled artisan, the present invention contemplates compositions comprising from about 50 μg to about 2000 μg of adjuvant and preferably about 250 μg/ml dose of the vaccine composition. Thus, the immunogenic composition as used herein also refers to a composition that comprises from about 1 μg/ml to about 60 μg/ml of antibiotics, and more preferably less than about 30 μg/ml of antibiotics.

The immunogenic composition as used herein also refers to a composition that comprises (i) any of the polypeptides of the present invention described above, preferably in concentrations described above; (ii) at least a portion of the viral vector expressing said polypeptide of the present invention; (iii) a portion of the cell culture; (iv) an inactivating agent to inactivate the recombinant viral vector, preferably BEI; and (v) an neutralization agent to stop the inactivation mediated by the inactivating agent, preferably sodium thiosulfate in equivalent amounts to BEI; (vi) a suitable adjuvant, preferably CARBOPOL® 971 in amounts described above; (vii) a pharmaceutical acceptable concentration of a saline buffer, preferably of a phosphate salt; and (viii) an anti-microbiological active agent; wherein about 90% of the components (i) to (iii) have a size smaller than 1 μm.

For investigation of a possible interference of the polypeptide of the present invention with the maternal antibody a study may be conducted in which the antibody titers of study animals are determined at the time of vaccination which are then grouped into a low, moderate and high antibody class: Geometric mean titers of <1:100 are considered as low antibody titers, titers of 1:100 to 1:1000 are considered as moderate antibody titers and titers of >1:1000 are considered as high antibody titers. This grouping pattern is comparable to that done in a Canadian field study where antibody titers of 1:80 were considered as low, antibody titers of 1:640 as moderate and antibody titers of >1:1280 as high (Larochelle et al., 2003, Can. J. Vet. Res.; 67: 114-120). In order to analyze the impact of low, medium and high antibody titers at the time of vaccination on viremia, vaccinated and placebo-treated animals are compared with regard to the onset, end, duration of viremia, the number of positive sampling days and the virus load. The presence of anti-PCV2 antibodies, in particular of maternal derived antibodies, preferably has no significant impact of any of those parameters. In other words, the efficacy of the polypeptide of the present invention in prevention and treatment of a PCV2 infection or in reduction of clinical signs caused by or associated with a PCV2 infection in animals is preferably not affected at the day of vaccination by the presence of anti-PCV2 antibodies, preferably by anti-PCV2 antibody titers of up to 1:100, preferably of more than 1:100, even more preferably of more than 1:250, even more preferably of more than 1:500, even more preferably of 1:640; even more preferably of more than 1:750, most preferably of more than 1:1000. This effect may be shown in a one shot vaccination experiment, which means that the polypeptide of the present invention is administered only once and without any subsequent administration of the polypeptide of the present invention.

Methods for detection and quantification of anti-PCV2 antibodies are well known in the art. For example detection and quantification of PCV2 antibodies can be performed by indirect immunofluorescence as described in Magar et al., 2000, Can. J. Vet Res.; 64: 184-186 or Magar et al., 2000, J. Comp. Pathol.; 123: 258-269. Further assays for quantification of anti-PCV2 antibodies are described in Opriessnig et al., 2006, 37th Annual Meeting of the American Association of Swine Veterinarians. Moreover, an indirect immunofluorescence assay, that may be used by a person skilled in the art comprises the steps of: seeding about 20.000 to 60.000 PK15 or VIDO R1 cells per well onto a 96 well plate; infecting cells with a PCV2 isolate, when monolayers are approximately 65 to 85% confluent; incubating infected cells for 48 hours; removing medium and washing cells 2 times with PBS; discarding the wash buffer and treating cells with cold 50/50 methanol/acetone fixative (~100 µl/well) for about 15 min at about −20° C.; discarding the fixative and air drying of the plates; preparing serial dilutions of porcine serum samples in PBS and serial dilutions of an anti-PCV2 positive and negative control sample (Positive Control and Negative Control Samples); adding the serial dilutions to the plates and incubating to allow antibodies to bind if present in the serum samples for about 1 hr. at 36.5±1° C.; washing the plates three times with PBS an discarding the PBS; staining the plates with a commercial Goat anti-Swine FITC conjugate diluted 1:100 in PBS and incubated for about 1 hr. at 36.5±1° C.; removing microplates are removed from incubator, the conjugate is discarded and the plates are washed 2 times with PBS; reading the plates using UV microscopy and reporting individual wells as positive or negative, wherein the Positive Control and Negative Control samples are used to monitor the test system; and calculating the serum antibody titers using the highest dilution showing specific IFA reactivity and the number of wells positive per dilution, or a 50% endpoint is calculated using the appropriate Reed-Muench formula.

Such an assay is described in Example 2 of WO 2008/076915 A2, hereby incorporated by reference.

In cases of controversial results and in any question of doubt, anti-PCV2 titers as mentioned herein, refer to those which are/can be estimated by this assay.

Thus according to a further aspect, the present invention provides a method for the treatment or prevention of a PCV2 infection or for reduction of clinical signs caused by or associated with a PCV2 infection in animals, preferably animals having anti-PCV2 antibodies, in particular maternal antibodies, comprising the step of administering an effective amount of a polypeptide of the present invention to that animal in need of such treatment, preferably of less than 20 µg/dose wherein said animal have a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000. Preferably, the anti-PCV2 antibody titer is detectable and quantifiable in a specific anti-PCV2 immune assay, preferably in the assay as described above, as exemplarily described in Example 2 of WO 2008/076915 A2. More preferably, those anti-PCV-2 antibodies are maternal derived antibodies. Most preferably, the polypeptide of the present invention is only administered once, preferably with a dose of less than 20 µg/dose.

Piglets with only low titers (<1:100) or moderate titers (<1:1000) of maternal derived anti-PCV2 antibodies are not sufficiently protected against PCV2 infections which occur prior to week 3 of age. Therefore, vaccination at a very early stage of life is desirable. Within the context of the invention, vaccination/treatment of animals at or before 3 weeks of age is preferred. Moreover, anti-PCV2 antibody titers of more than 1:1000 preferably have no influence on the efficacy of the PCV2 vaccine regardless of the level of the existing initial antibody titer. For example, vaccination of high-titer animals (anti-PCV2 antibody titer >1:1000) preferably result in a shorter duration of viremia, an earlier end of viremia, less viremic sampling days and a reduction of the sum of genomic equivalents/ml as compared to non-vaccinated control animals. Upon comparison of vaccinated "high", "moderate" and "low titer animals" no significant differences are preferably observed with regard to the different parameters of PCV2 viraemia. Also in the presence of high anti-PCV2 antibody titers the polypeptide of the present invention used for vaccination preferably still significantly reduces viremia in blood (e.g., end of viremia, duration of viremia, virus load). Preferably, no differences are found with regard to the live body weight when comparing low and high titer animals of the vaccinated group. Furthermore, vaccinated animals with a high anti-PCV2 antibody titer at the time of vaccination/treatment (>1:1000) also preferably show a significantly higher body weight after the onset of viremia compared to placebo-treated animals with initial high antibody titers. Consequently, according to a preferred aspect, vaccination/treatment of animals of 1 day of age or older with the polypeptide of the present invention is possible. However, vaccination should be done within the first 8, preferably within the first 7 weeks of age. Thus according to a further aspect, the present invention provides a method for the treatment or prevention of a PCV2 infection or for reduction of clinical signs caused by or associated with a PCV2 infection in animals, comprising the step of administering to that animal in need of such treatment at day 1 of age or later, preferably but not later than at week 8 of age an effective amount of the polypeptide of the present invention. According to a preferred embodiment, less than 20 µg/dose polypeptide of the present invention are required to confer immunity in such animal. According to a more preferred embodiment, the polypeptide of the present invention, preferably less than a 20 µg/dose thereof is only administered once to the animal in need of such treatment.

According to a further, more general aspect, the present invention provides a method for the treatment or prevention of a PCV2 infection or for reduction of clinical signs caused by or associated with a PCV2 infection in young animals, comprising the step of administering an effective amount of the polypeptide of the present invention to that animal in need of such treatment.

The term "young animal" as used herein refers to an animal of 1 to 22 days of age. Preferably, by the term young animal, an animal of 1 to 20 days of age is meant. More preferably, the term young animal refers to an animal of 1 to 15 days of age, even more preferably of 1 day of age to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably to an animal of 1 day of age.

Thus according to a further aspect, the present invention provides a method for the treatment or prevention of a PCV2 infection or for reduction of clinical signs caused by or associated with a PCV2 infection in young animals, comprising the step of administering an effective amount of the polypeptide of the present invention to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably at 1 day of age in need of such treatment. For example, the vaccination/treatment on 19 to 22 days of age preferably shows high efficacy of vaccination. Moreover, vaccination/treatment at 12 to 18, preferably 12 to 14 days of age is preferably very effective in reduction of clinical signs associated with PCV2 infections, reduction of overall viral load, reduction of duration of viremia, delay in onset of viremia, weight gain. Moreover, vaccination at 1 week of age is preferably very effective in reduction of clinical signs associated with PCV2 infections, reduction of overall viral load, reduction of duration of viremia, delay in onset of viremia, weight gain. Preferably less than 20 µg/dose of the polypeptide of the present invention is required to confer immunity in those young animals. According to a more preferred embodiment, the polypeptide of the present invention, preferably less than 20 µg is only administered once to that young animal in need of such treatment.

Due to the ubiquity of PCV2 in the field most of the young piglets are seropositive in respect to PCV2. Thus according to a further aspect, the present invention provides a method for the treatment or prevention of a PCV2 infection or for reduction of clinical signs caused by or associated with a PCV2 infection in young animals, preferably animals having anti-PCV2 antibodies at the day of vaccination, comprising the step of administering an effective amount of the polypeptide of the present invention to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably at 1 or 2 day(s) of age, most preferably at 1 day of age in need of such treatment.

Preferably, said young animals, at the day of vaccination/treatment, have a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000 at the day of vaccination/treatment. Preferably less than 20 µg/dose of the polypeptide of the present invention are required to confer a sufficient immunity in those young animals. According to more preferred embodiment, the polypeptide of the present invention, preferably less than 20 µg is only administered once to that young animal in need of such treatment.

As described above, vaccination/treatment of young animals with the polypeptide of the present invention preferably results in shortening of viremic phase as compared to non-vaccinated control animals. The average shortening time may preferably, for instance, be 9.5 days as compared to non-vaccinated control animals of the same species. Therefore, according to a further aspect, the present invention also provides a method for the treatment or prevention of a PCV2 infection or for reduction of clinical signs caused by or associated with a PCV2 infection in young animals, comprising the step of administering an effective amount of the polypeptide of the present invention to that animal in need of such treatment, wherein the treatment or prevention results in shortening of the viremia phase of 5 or more days, preferably 6 or more days, even more preferably of 7 or more days, even more preferably of 8 or more days, even more preferably of 9, even more preferably of 10, even more preferably of 12, even more preferably of 14, most preferably of more than 16 days as compared to animals of a non-treated control group of the same species. In some cases, the viremic phase is preferably shortening for more than 20 days. In general, the vaccination of young piglets preferably results in a reduction in the loss of weight gain, a shorter duration of viremia, an earlier end to viremia, and a lower virus load. Therefore, according to a further aspect, the present invention provides a method for the treatment or prevention of a PCV2 infection or for reduction of clinical signs caused by or associated with a PCV2 infection in young animals, comprising the step of administering an effective amount of the polypeptide of the present invention to that animal in need of such treatment, wherein said treatment or prevention of PCV2 infection results in an improvement in comparison to animals of a non-treated control group of the same species in a vaccine efficacy parameter selected from the group consisting of a reduction in the loss of weight gain, a shorter duration of viremia, an earlier end to viremia, a lower virus load, or combinations thereof. Preferably less than 20 µg/dose polypeptide of the present invention are required to cause any of the improved vaccine efficacy parameter mentioned above. Moreover such improved vaccine efficacy parameter are achieved by a singly administration of only one dose.

The term "an effective amount" as used herein means but is not limited to an amount of the polypeptide of the present invention, that elicits or is able to elicit an immune response in an animal, to which said effective dose of the polypeptide of the present invention is administered. Preferably, an effective amount is defined as an amount of the polypeptide of the present invention that confers at least a 10 weeks duration of immunity (DOI), preferably at least a 12 weeks (DOI), more preferably at least a 15 weeks (DOI), most preferably at least a 20 weeks (DOI).

The amount that is effective depends on the ingredients of the vaccine and the schedule of administration. Typically, when an inactivated virus or a modified live virus preparation is used in the combination vaccine, an amount of the vaccine containing about $10^{2.0}$ to about $10^{9.0}$ TCID$_{50}$ per dose, preferably about $10^{3.0}$ to about $10^{8.0}$ TCID$_{50}$ per dose, more preferably, about $10^{4.0}$ to about $10^{8.0}$ TCID$_{50}$ per dose. In particular, when modified live PCV2 is used in the vaccines, the recommended dose to be administered to the susceptible animal is preferably about $10^{3.0}$ TCID$_{50}$ (tissue culture infective dose 50% end point)/dose to about $10^{6.0}$ TCID$_{50}$/dose and more preferably about $10^{4.0}$ TCID$_{50}$/dose to about $10^{5.0}$ TCID$_{50}$/dose. In general, the quantity of antigen will be between 0.2 and 5000 micrograms, and between $10^{2.0}$ and $10^{9.0}$ TCID$_{50}$, preferably between $10^{3.0}$ and $10^{6.0}$ TCID$_{50}$, more preferably between $10^{4.0}$ and $10^{5.0}$ TCID$_{50}$, when purified antigen is used.

Sub-unit vaccines are normally administered with an protein inclusion level of at least 0.2 µg protein per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.5 to about 18 µg/dose, still more preferably with about 0.6 to about 16 µg/dose, even more preferably with about 0.75 to about 8 µg/dose, even more preferably with about 1.0 to about 6 µg/dose, still more preferably with about 1.3 to about 3.0 µg/dose.

Preferably, the prophylactic use of the immunogenic compositions described supra, is effective for reduction of clinical signs caused by or associated with PCV2 infections, preferably in young animals and/or in animals having passive immunity against PCV2 at the day of treatment. In particular, the prophylactic use of the immunogenic compositions as described herein, and specifically of compositions comprising the polypeptide of the present invention, is preferably effective for reducing lymphadenopathy, lymphoid depletion and/or multinucleated/giant histiocytes in animals infected with PCV2 and having maternal anti-PCV-2 antibodies at the day of treatment/vaccination. For example it was discovered that the prophylactic use of the immunogenic compositions as described herein is effective for reducing lymphoid depletion, lymphoid inflammation, positive IHC for PCV2 antigen of lymphoid tissue, viremia, nasal shedding, pyrexia, reduced average daily weight gain, lung inflammation, positive IHC for PCV2 antigen of lung tissue.

Furthermore, the prophylactic use of the immunogenic compositions as described herein is preferably effective for reducing (1) interstitial pneumonia with interlobular edema, (2) cutaneous pallor or icterus, (3) mottled atrophic livers, (4) gastric ulcers, (5) nephritis, (6) reproductive disorders, e.g., abortion, stillbirths, mummies, etc., (7) Pia like lesions, normally known to be associated with *Lawsonia intracellularis* infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability, (15), reduced frequency of 'runts', (16) reduced co-infections with Porcine Reproductive and Respiratory Disease Complex (PRRSV). Such immunogenic composition is also effective in improving economically important growth parameters such as time to slaughter, carcass weight, and lean meat ratio. Thus the term "clinical signs" as used herein, means, but is not limited to (1) interstitial pneumonia with interlobular edema, (2) cutaneous pallor or icterus, (3) mottled atrophic livers, (4) gastric ulcers, (5) nephritis and (6) reproductive disorders, e.g., abortion, stillbirths, mummies, etc., (7) Pia-like lesions, normally known to be associated with *Lawsonia intracellularis* infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15) reduced frequency of 'runts', (16) reduced co-infections with Porcine Reproductive and Respiratory Disease Complex (PRRSV), (17) lymphoid inflammation, (18) positive IHC for PCV2 antigen of lymphoid tissue, (19) viremia, (20) nasal shedding, (21) pyrexia, (22) reduced average daily weight gain, (23) lung inflammation, (24) positive IHC for PCV2 antigen of lung tissue. Moreover, the immunogenic composition described herein reduces the overall circovirus load including a later onset, a shorter duration, an earlier end of viremia, and a reduced viral load and its immunosuppressive impact in young animals, in particular in those having anti-PCV2 antibodies at the day of vaccination, thereby resulting in a higher level of general disease resistance and a reduced incidence of PCV2 associated diseases and clinical signs.

Thus, according to a further aspect, the present invention provides a method for the treatment or prevention of a PCV2 infection or for reduction of clinical signs caused by or associated with a PCV2 infection in young animals and/or in animals, preferably animals having anti-PCV2 antibodies, comprising the step of administering an effective amount of the polypeptide of the present invention or an immunogenic composition comprising the polypeptide of the present invention to that animal in need of such treatment, wherein those clinical signs are selected from the group consisting of: (1) interstitial pneumonia with interlobular edema, (2) cutaneous pallor or icterus, (3) mottled atrophic livers, (4) gastric ulcers, (5) nephritis, (6) reproductive disorders, e.g. abortion, stillbirths, mummies, etc., (7) Pia-like lesions, normally known to be associated with *Lawsonia intracellularis* infections (Ileitis), (8) lymphadenopathy, (9) lymphoid depletion and/or (10) multinucleated/giant histiocytes, (11), Porcine Dermatitis and Nephropathy Syndrome (PDNS), (12) PCVAD associated mortality, (13) PCVAD associated weight loss, (14) reduced growth variability, (15) reduced frequency of 'runts', (16) reduced co-infections with Porcine Reproductive and Respiratory Disease Complex (PRRSV), (17) lymphoid inflammation, (18) positive IHC for PCV2 antigen of lymphoid tissue, (19) viremia, (20) nasal shedding, (21) pyrexia, (22) reduced average daily weight gain, (23) lung inflammation, (24) positive IHC for PCV2 antigen of lung tissue. According to a further aspect, the present invention provides a method for the treatment or prevention of a PCV2 infection or for reduction of clinical signs caused by or associated with a PCV2 infection in young animals, comprising the step of administering an effective amount of the polypeptide of the present invention to that animal in need of such treatment, wherein those clinical signs are selected from the group consisting of: (1) interstitial pneumonia with interlobular edema, (2) cutaneous pallor or icterus, (3) mottled atrophic livers, (4) gastric ulcers, (5) nephritis, (6) reproductive disorders, e.g., abortion, stillbirths, mummies, etc., (7) Pia-like lesions, normally known to be associated with *Lawsonia intracellularis* infections (Ileitis), (8) lymphadenopathy, (9) lymphoid depletion and/or (10) multinucleated/giant histiocytes, (11) Porcine Dermatitis and Nephropathy Syndrome (PDNS), (12) PCVAD associated mortality, (13) PCVAD associated weight loss, (14) reduced growth variability, (15) reduced frequency of 'runts', (16) reduced co-infections with Porcine Reproductive and Respiratory Disease Complex (PRRSV), (17) lymphoid inflammation, (18) positive IHC for PCV2 antigen of lymphoid tissue, (19) viremia, (20) nasal shedding, (21) pyrexia, (22) reduced average daily weight gain, (23) lung inflammation, (24) positive IHC for PCV2 antigen of lung tissue.

The composition according to the invention may be applied, orally, intradermally, intratracheally, or intravaginally. The composition preferably may be applied intramuscularly or intranasally, most preferably intramuscularly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (e.g., connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

Preferably, one dose of the immunogenic composition as described above is intramuscularly administered to the subject in need thereof. According to a further aspect, the polypeptide of the present invention or the immunogenic composition comprising any such polypeptide of the present invention as described herein is bottled in and administered at one (1) mL per dose. Thus, according to a further aspect, the present invention also provides a 1 ml immunogenic composition, comprising the polypeptide of the present invention as described herein, for the treatment or prevention of a PCV2 infection or for reduction of clinical signs caused by or associated with a PCV2 infection in young animals, comprising the step of administering an effective amount of the polypeptide of the present invention protein to that animal in need of such treatment. According to a further aspect, the present invention also provides a 1 ml immunogenic composition, comprising the polypeptide of the present invention as described herein, for the treatment or prophylaxis of a PCV2 infection or for reduction of clinical signs caused by or associated with a PCV2 infection in animals, preferably animals having anti-PCV2 antibodies, comprising the step of administering an effective amount of the polypeptide of the present invention or an immunogenic composition comprising the polypeptide of the present invention to that animal in need of such treatment.

According to a further aspect, at least one further administration of at least one dose of the immunogenic composition as described above is given to a subject in need thereof, wherein the second or any further administration is given at least 14 days beyond the initial or any previous administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant. Preferably, the immune stimulant is given at least 10 days, preferably 15 days, even more preferably 20, even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

In a further aspect, the invention provides a method of determining whether an individual has received an immunogenic composition, in particular a vaccine, containing the polypeptide of the present invention, wherein said method, comprises the steps of:

obtaining a biological sample from an individual, and determining in said biological sample the presence or absence of one or more markers showing that the individual has received the amino acid sequence of interest included in the polypeptide of the present invention, and wherein the presence of said one or more markers in said biological sample indicates that said individual has received said immunogenic composition or wherein the absence of said one or more markers in said biological sample indicates that said individual has not received said immunogenic composition.

According to said first aspect, the present invention hence provides a method of determining whether an individual has received an immunogenic composition comprising the polypeptide of the present invention, said method also being termed "the method of the present invention" hereinafter, wherein said method in particular comprises determining in a biological sample obtained from said individual the presence or absence of one or more markers showing that the individual has received said amino acid sequence of interest, and wherein the presence of said one or more markers in said biological sample indicates that said individual has received said immunogenic composition.

Preferably, the immunogenic composition of the present invention is a marker vaccine, in particular a positive marker vaccine.

The term "marker vaccine" as described herein, in particular specifies a vaccine leading to an immunization in the immunized organism, which differs from the immunization of the organism caused by the real pathogen.

A "positive marker vaccine" particularly relates to a marker vaccine containing an additional antigen which induces the production of specific antibodies present in vaccinated individuals but not in infected ones.

The term "marker" as used within the context of the present invention is preferably equivalent to the term "biomarker", and in particular refers to a measurable substance or compound which indicates that an individual has been exposed to an immunogenic composition, preferably to a positive marker vaccine or, more particular, to the additional antigen of a positive marker vaccine which induces the production of specific antibodies found in vaccinated subjects but not in infected ones.

As used herein, the term "immunogenic composition" in particular refers to a composition that will elicit an immune response in an individual that has been exposed to the composition. An immune response may include induction of antibodies and/or induction of a T-cell response. Depending on the intended function of the composition, one or more antigens may be included. Preferably, the immunogenic composition as described herein is a vaccine.

The term "vaccine" as used herein, is in particular defined in accordance with the pertinent art and relates to a composition that induces or enhances immunity of an individual to a particular disease. To this end, the vaccine comprises a compound that is similar to the pathogen or a compound of said pathogen causing said disease. Upon contact with this compound, the immune system of the individual is triggered to recognize the compound as foreign and to destroy it. The immune system subsequently "remembers" the contact with this compound, so that at a later contact with the disease-causing pathogen an easy and efficient recognition and destruction of the pathogen is ensured. In accordance with the present invention, the vaccine may be in any formulation for vaccines known in the art, such as for example vaccines for intramuscular injection, mucosal vaccines or vaccines for subcutaneous or intradermal injection as well as vaccines for inhalation, such as e.g., as aerosols. Such vaccine formulations are well known in the art and have been described, e.g., in Neutra M R et al. 2006 Mucosal vaccines: the promise and the challenge 6(2): 148-58 or F. P. Nijkamp, Michael J. Parnham 2011; Principles of Immunopharmacology ISBN-13: 978-3034601351.

Preferably, the biological sample is obtained from said individual 14 to 35 days after the day the individual has been vaccinated or, respectively, has been supposedly vaccinated.

The one or more markers showing that the individual has received the amino acid sequence of interest, which are also termed "the one or more markers of the present invention" hereinafter, are antibodies specific for said amino acid sequence of interest.

Preferably, the antibodies as described herein are polyclonal antibodies.

As used herein, the term "antibodies specific for" a defined antigen in particular refers to antibodies, preferably polyclonal antibodies, that bind an antigen with an affinity or $K_a$ (i.e., an equilibrium association constant of a particular binding interaction with units of 1/M) of, for example, greater than or equal to about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. Alternatively, binding affinity may be defined as an equilibrium dissociation constant ($K_d$) of a particular binding interaction with units of M (e.g., $10^{-5}$ M to $10^{-13}$ M). Binding affinities of antibodies can be readily determined using techniques well known to those of skill in the art (see, e.g., Scatchard et al. (1949) Ann. N.Y. Acad. Sci. 51:660; U.S. Pat. Nos. 5,283,173; 5,468,614; BIACORE® analysis; or the equivalent).

Preferably, the method of the present invention comprises the steps of:
  contacting the biological sample with a capture reagent immobilized to a solid support, wherein the immobilized capture reagent is capable of binding said one or more markers, and
  determining the presence or absence of said one or more markers bound to the capture reagent, wherein the presence of said one or more markers bound to the capture reagent is indicative for the presence of said one or more markers in said biological sample.

The term "capture reagent", as used herein, in particular refers to a molecule or a multi-molecular complex that can bind to a marker. The capture reagent is preferably capable of binding the marker in a substantially specific manner, preferably with an affinity or $K_a > 10^5$ $M^{-1}$ or preferably $>10^6$ $M^{-1}$. The capture reagent may optionally be a naturally occurring, recombinant, or synthetic biomolecule. Proteins and nucleic acid ligands (aptamers) are highly suitable as capture agents. A whole virus or a virus fragment or a synthetic peptide may also serve as preferred capture reagents, since they are capable of binding antibodies.

The herein mentioned capture reagent being immobilized to a solid support and being capable of binding one or more markers of the present invention, wherein said capture reagent is also termed "capture reagent according to the present invention" hereinafter, is preferably (i) a protein comprising the amino acid sequence of interest or (ii) a peptide, e.g., a synthetic peptide, comprising or consisting of the amino acid sequence of interest.

As used herein the term "immobilized" particularly means that the capture reagent can be attached to a surface (e.g., the solid support) in any manner or any method; including, e.g., reversible or non-reversible binding, covalent or non-covalent attachment, and the like.

The term "solid support", as mentioned herein, denotes a non-fluid substance, and includes chips, vessels, and particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid support component of an assay is distinguished from inert solid surfaces with which the assay may be in contact in that a "solid support" contains at least one moiety on its surface, which is intended to interact with the capture reagent, either directly or indirectly. A solid support may be a stationary component, such as a tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly(methyl methacrylate); gold particles such as gold nanoparticles and gold colloids; and ceramic particles such as silica, glass, and metal oxide particles. See for example Martin, C. R., et al., Analytical Chemistry-News & Features 70 (1998) 322A-327A, which is incorporated herein by reference.

A "chip" is a solid, non-porous material, such as metal, glass or plastics. The material may optionally be coated, entirely or in certain areas. On the surface of the material any array of spots is present, either visible or in coordinates. On each spot a defined polypeptide, with or without linker or spacer to the surface of the material, may be immobilized. All documents mentioned herein, both supra and infra, are hereby incorporated herein by reference.

Preferably, the method of the present invention comprises determining in the biological sample the presence or absence of the one or more markers of the present invention, wherein said markers are antibodies specific for said amino acid sequence of interest, and wherein said method comprises the steps of:
  a. contacting the biological sample with a capture reagent immobilized to a solid support, wherein the capture reagent is selected from the group consisting of
    i. a protein comprising the amino acid sequence of interest,
    ii. a peptide comprising or consisting of the amino acid sequence of interest;
  b. separating the biological sample from the immobilized capture reagent;
  c. contacting the immobilized capture reagent-antibody complex with a detectable agent that binds to the antibody of the reagent-antibody complex; and
  d. measuring the level of antibody bound to the capture reagent using a detection means for the detectable agent, and wherein the measuring step (D) preferably further comprises a comparison with a standard curve to determine the level of antibody bound to the capture reagent.

Preferably, said detectable agent that binds to the antibody of the reagent-antibody complex is a detectable antibody, more preferably a labelled secondary antibody.

The method of the present invention preferably further comprises the step of determining in the biological sample the presence of one or more analytes selected from the group consisting of:

antibodies specific for a polypeptide which comprises or consists of an amino acid sequence having at least 90% sequence identity with the amino acid sequence of SEQ ID NO:2 or SEQ ID NO:3.

Within the context of the method of the present invention, the immunogenic composition is preferably the immunogenic composition as described underneath.

The term "biological sample" as used herein refers to any sample that is taken from an individual (e.g., from a pig or a bird) and includes, without limitation, cell-containing bodily fluids, peripheral blood, blood plasma or serum, saliva, tissue homogenates, lung and other organ aspirates, and lavage and enema solutions, and any other source that is obtainable from a human or animal subject. For animals, examples of a "biological sample" include blood, cells, feces, diarrhea, milk, mucus, phlegm, pus, saliva, semen, sweat, tear, urine, tears, ocular fluids, vaginal secretions, and vomit, if present in that animal.

The biological sample, as referred to herein, has preferably been isolated from a pig and/or is particular selected from the group consisting of whole blood, blood plasma, serum, urine, and oral fluids. Herein, the term "serum" is meant to be equivalent to "blood serum".

The term "oral fluids" as used herein, in particular refers to one or more fluids found in the oral cavity, individually or in combination. These include, but are not limited to saliva and mucosal transudate. It is particularly understood that oral fluids can comprise a combination of fluids from a number of sources (e.g., parotid, submandibular, sublingual, accessory glands, gingival mucosa and buccal mucosa) and the term "oral fluids" includes the fluids from each of these sources individually, or in combination. The term "saliva" refers to a combination of oral fluids such as is typically found in the mouth, in particular after chewing. The term "mucosal transudate", as used herein, refers to fluid produced by the passive diffusion of serum components from oral mucosal interstitia into the oral cavity. Mucosal transudate often forms one component of saliva.

The immobilized capture reagent, as described herein, is preferably coated on a microtiter plate, in particular to a microtiter plate capable to be read out by an ELISA reader.

According to still another aspect, the present invention provides a kit, in particular a test kit, for determining whether an individual has received an immunogenic composition containing the polypeptide of the present invention, wherein said kit contains one or more capture reagents immobilized to a solid support, wherein the one or more immobilized capture reagents are capable of binding antibodies specific for the amino acid sequence of interest contained in the polypeptide of the present invention, and wherein the one or more capture reagents is preferably selected from the group consisting of i. a protein comprising the amino acid sequence of interest; and ii. a peptide, in particular a synthetic peptide, comprising or consisting of the amino acid sequence of interest.

EXAMPLES

Example 1

Materials & Procedure/Design of Mutants
Preparation of Mutant PCV2b ORF2 Baculovirus The sequence encoding SEQ ID NO: 1 (PCV2b ORF2-cmyc) was cloned into baculovirus transfer vector pVL1393 and co-transfected with baculovirus DNA in Sf9 cells. The resulting recombinant baculovirus was checked for PCV2b ORF2-cmyc expression by IFA. Amplified stocks of the recombinant baculovirus were prepared on Sf+ cells and titrated via the $TCID_{50}$ method to determine the baculoviral titer.

Expression Evaluation of PCV2b ORF2-Cmyc Baculovirus

Figure 2:
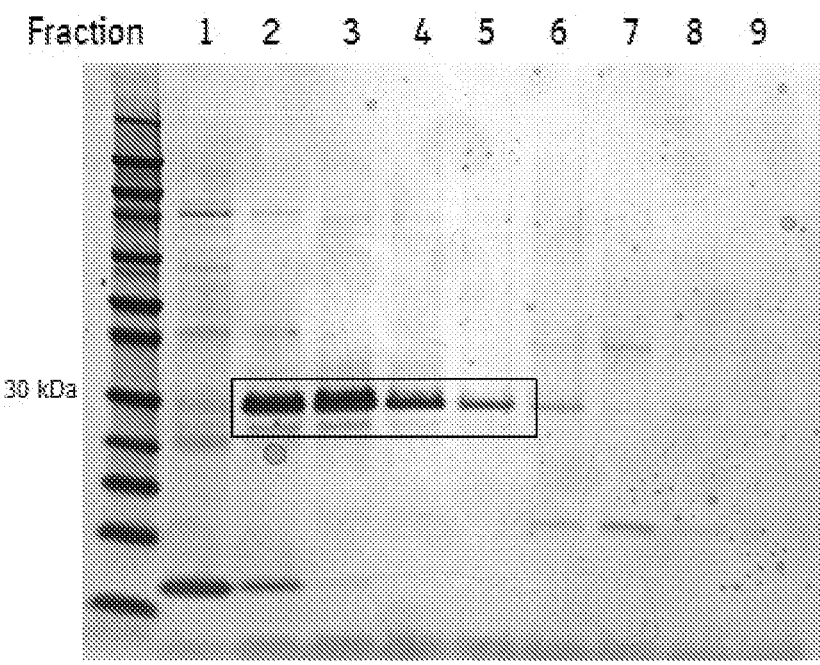
FIG. 2. Harvests of BaculoG/PCV2b ORF2 c-myc were centrifuged at 100,000 g for two hours at 4° C. to pellet the VLPs. Resuspended pellets were separated on a 10%-60% discontinuous sucrose gradient by centrifugation at 100,000 g for two hours at 4° C. to partially purify the PCV2b ORF2-cmyc proteins for quantitation and VLP confirmation by electron microscopy (EM). The sucrose gradient was fractionated into 9 fractions and separated by SDS-PAGE where the majority of the PCV2b ORF2-c-myc was detected in the fractions expected for PCV2b ORF2 VLPs.

The recombinant baculovirus was evaluated for expression of its PCV2b ORF2-cmyc coding sequence by infecting Sf+ cells at a target MOI of 0.1. The infections were allowed to progress for 5-7 days then were harvested by centrifugation at 20,000 g for 20 min to remove cellular debris and insoluble protein. The harvest supernatants were 0.2 µm filtered and evaluated directly for PCV2b ORF2-cmyc expression by western blot using α-PCV2 antibodies. The harvest supernatants were also evaluated for the presence of macromolecular structures. Briefly, a sample of each harvest supernatant was centrifuged at 100,000 g for two hours. The resulting pellets were resuspended in a small volume of TBS and separated by SDS-PAGE. PCV2b ORF2-cmyc bands were detected in stained gels by size comparison to PCV2b ORF2 (FIG. 1). Resuspended pellets were also separated on a 10%-60% discontinuous sucrose gradient by centrifugation at 100,000 g for two hours to partially purify the PCV2b ORF2-cmyc proteins for quantitation and VLP confirmation by electron microscopy (EM) (FIG. 2).

Figure 3:
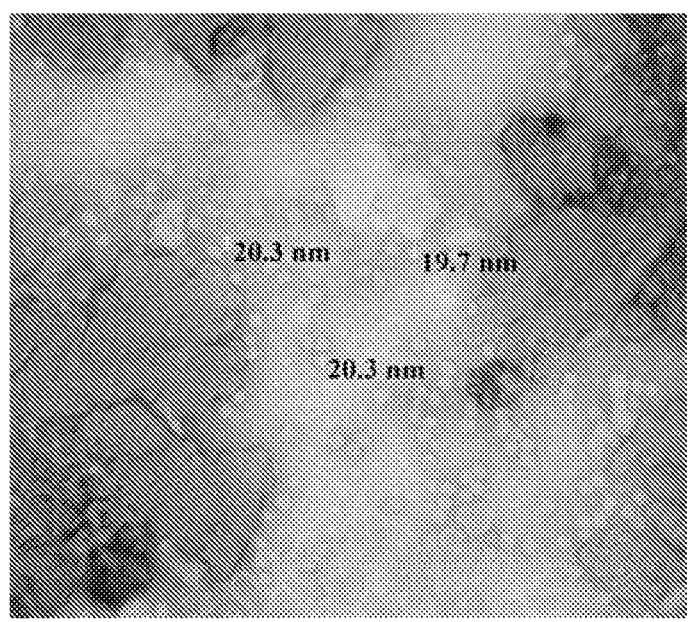
FIG. 3. The PCV2b ORF2-c-myc-containing fractions (boxed from FIG. 2) were pooled and a sample of the sucrose gradient-purified material concentrated and submitted for VLP confirmation by EM using phosphotungstic acid as a negative stain.

After sucrose gradient separation, the PCV2b ORF2 containing fractions were pooled and the PCV2b ORF2-cmyc concentration was determined by SDS-PAGE gel densitometry compared to a BSA standard curve. In addition, a sample of the sucrose gradient-purified material was further concentrated and submitted for VLP confirmation by EM using phosphotungstic acid as a negative stain (e.g., FIG. 3).

Example 2

By means of ELISA the produced PCV2b ORF2-cmyc was tested for recognition by (i) an anti PCV2b ORF2 antibody and (ii) an anti-c-myc antibody.

Figure 4:
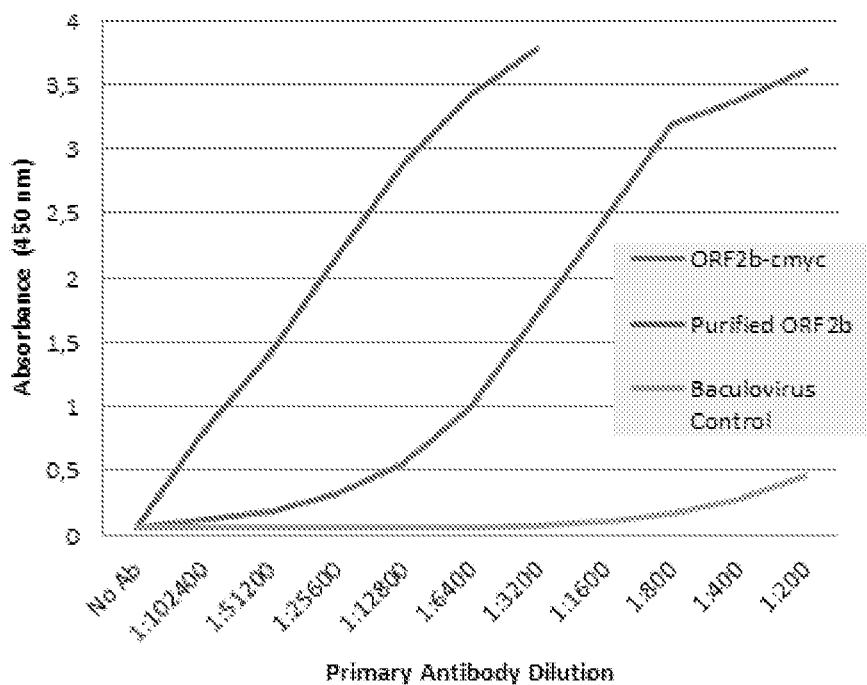
FIG. 4. ELISA plates were coated with PCV2b ORF2-c-myc VLPs, PCV2b ORF2 VLPs or Baculovirus control antigen and probed with serial dilutions of antibodies A. swine anti-PCV2b antibody or B. mouse anti-c-myc mAb 9E10. Anti-PCV2b antibody recognized both PCV2b ORF2 VLPs and PCV2b ORF2-c-myc VLPs while anti-c-myc antibody only recognized PCV2b ORF2-c-myc VLPs.
Figure 4:
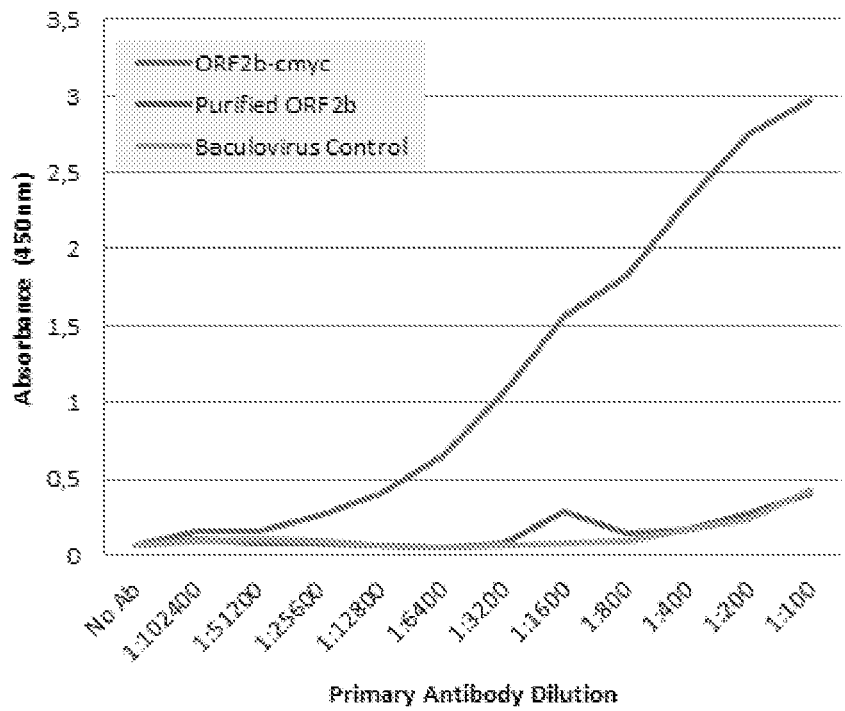

As result, it was seen that PCV2 ORF2-c-myc VLPs were recognized by both anti-PCV2b ORF2 antibody and anti-c-myc antibody (FIG. 4).

Example 3

Figure 5:
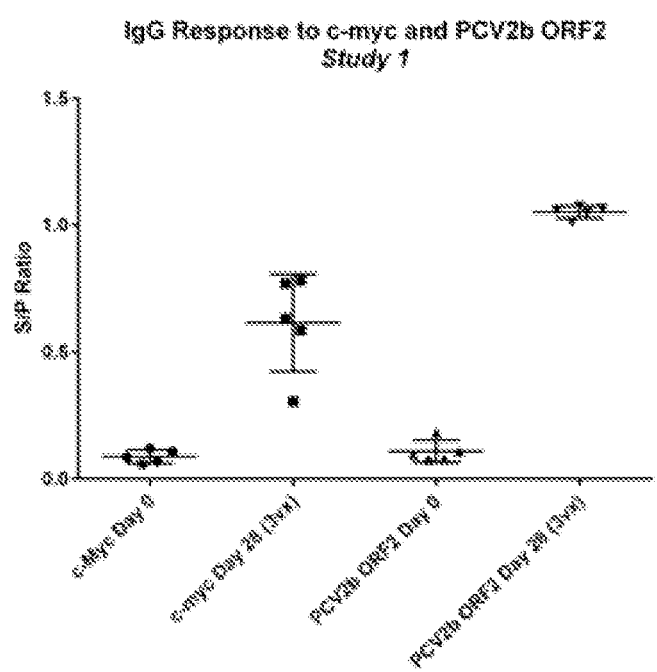
FIG. 5. Rabbits were vaccinated with purified PCV2b ORF2-c-myc VLPs formulated with Freund's adjuvant. The resulting serum samples were evaluated for an IgG response to c-myc peptide and PCV2b ORF2 VLPs by ELISA. A. IgG Response to c-myc and PCV2b ORF2 after 3 vaccinations. All rabbits generated an IgG response to c-myc peptide and PCV2b ORF2 VLPs after 3 vaccinations. B. IgG Response to c-myc and PCV2b ORF2 after a single vaccination. Five out of six rabbits generated an IgG response to c-myc peptide after a single dose of vaccine while all six rabbits generated an IgG response to PCV2b ORF2 VLPs after the single dose.
Figure 5:
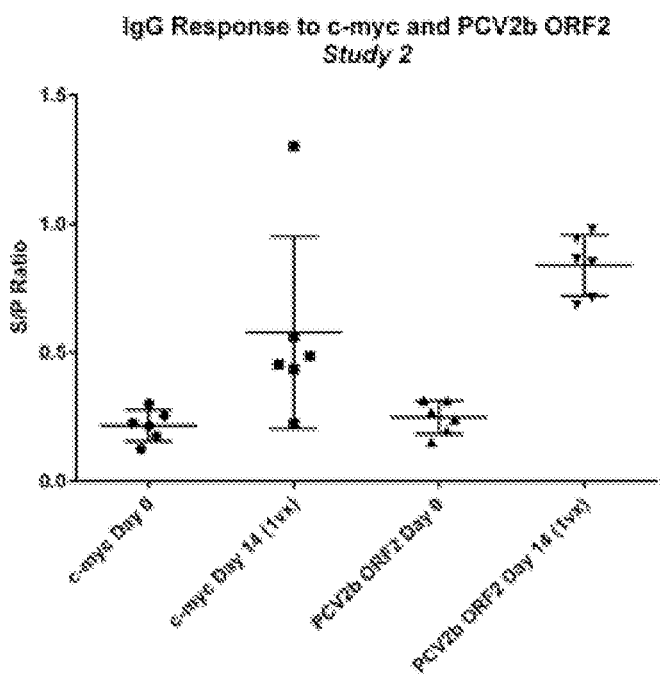

Purified PCV2 ORF2-c-myc VLPs were evaluated in rabbits according to the following schemes:
Study 1—200 µg/dose
 Day 0 (Freund's complete)
 Day 7 (Freund's incomplete)
 Day 14 (Freund's incomplete)
Study 2—200 µg/dose
 Day 0 (Freund's complete)
The serum samples were evaluated for IgG response to c-myc and PCV2 ORF2 by ELISA (FIG. 5).

IN THE SEQUENCE LISTING

SEQ ID NO: 1 corresponds to SEQ ID NO: 2 including SEQ ID NO: 6.
SEQ ID NO: 2 corresponds to the sequence of a wild type PCV2b ORF2 protein.
SEQ ID NO: 3 corresponds to the sequence of a wild type PCV2a ORF2 protein.
SEQ ID NO: 4 corresponds to a polynucleotide sequence encoding SEQ ID NO: 1.
SEQ ID NO: 5 corresponds to an amino acid sequence of interest comprising the c-myc tag peptide (corresponding to the C-terminal amino acids (410-419) of human c-myc protein).
SEQ ID NO: 6 corresponds to the sequence of a peptide encoded by the ORF5 gene of PRRS virus.

SEQ ID NO: 7 corresponds to the sequence of aa 1-11 of SEQ ID NO: 6.

What is claimed is:

1. A recombinant polypeptide selected from the group consisting of:
   a) a PCV2 ORF2 protein characterized in that at least one amino acid residue in the BC loop is replaced by an amino acid sequence of interest;
   b) a PCV2 ORF2 protein characterized in that an amino acid sequence of interest is inserted into the BC loop; or
   c) a combination of a) and b);
   wherein the amino acid sequence of interest comprises SEQ ID NO: 5 or 7.

2. The polypeptide of claim 1, wherein the BC loop is the region of the amino acid positions 58 to 66, and wherein the numbering of the amino acid positions refers to the amino acid sequence of wild type PCV2 ORF2 protein.

3. The polypeptide of claim 1, wherein the amino acid sequence of interest is an amino acid sequence comprising or consisting of at least eight amino acid residues.

4. The polypeptide of claim 1, wherein the amino acid sequence of interest comprises or consists of a heterologous amino acid sequence.

5. The polypeptide of claim 1, wherein a second amino acid sequence of interest is selected from the group consisting of an epitope of interest, a growth factor, a recognition sequence, a fusion protein, an antigen of interest, and/or a veterinary pathogen and/or toxin.

6. The polypeptide of claim 1, wherein the amino acid sequence of interest comprises or consists of an epitope of interest, and wherein the epitope of interest is an amino acid sequence comprising or consisting of 8 to 25 amino acid residues.

7. The polypeptide of claim 1, wherein in (a) at least one amino acid residue in the region of the amino acid positions 58 to 64 is replaced by an amino acid sequence of interest, and wherein the numbering of the amino acid positions refers to the amino acid sequence of wild type PCV2 ORF2 protein.

8. The polypeptide of claim 1, wherein in (a) at least two amino acid residues in the BC loop are replaced by an amino acid sequence of interest.

9. The polypeptide of claim 1, wherein in (a) two, three, four, five, six, or seven amino acid residues in the BC loop are replaced by an amino acid sequence of interest.

10. The polypeptide of claim 1, wherein
    i) six amino acid residues of the amino acid positions 58 to 63 of the BC loop are replaced by an amino acid sequence of interest, wherein the numbering of the amino acid positions refers to the amino acid sequence of wild type PCV2 ORF2 protein; and/or
    ii) the amino acid sequence of interest comprises or consists of an amino acid sequence consisting of 11 amino acid residues.

11. The polypeptide of claim 1, wherein said polypeptide is a recombinant baculovirus expressed protein.

12. The polypeptide of claim 1, wherein said PCV2 ORF2 protein is a PCV2 subtype b (PCV2b) ORF2 protein or a PCV2 subtype a (PCV2a) ORF2 protein and/or wherein said PCV2 ORF2 protein comprises or consists of an amino acid sequence having at least 90% sequence identity with the amino acid sequence of SEQ ID NO:2 or SEQ ID NO:3.

13. The polypeptide of claim 1, wherein said polypeptide comprises or consists of an amino acid sequence having at least 90% sequence identity with the amino acid sequence of SEQ ID NO: 1.

14. The polypeptide of claim 2, wherein said wild type PCV2 ORF2 protein is the protein set forth in SEQ ID NO:2 or SEQ ID NO:3.

15. An immunogenic composition containing the polypeptide of claim 1.

16. A polynucleotide comprising a sequence which encodes the polypeptide of claim 1.

17. A plasmid and/or an expression vector, which comprises a polynucleotide comprising a sequence which encodes the polypeptide of claim 1.

18. A cell comprising a plasmid and/or an expression vector, which comprises a polynucleotide comprising a sequence which encodes the polypeptide of claim 1.

19. A virus like particle composed of a plurality of the polypeptide of claim 1.

20. A baculovirus containing a polynucleotide comprising a sequence which encodes the polypeptide of claim 1.

21. A cell comprising a baculovirus which contains a polynucleotide comprising a sequence which encodes the polypeptide of claim 1.

22. Use of:
    a) a recombinant polypeptide selected from the group consisting of;
       i) a PCV2 ORF2 protein characterized in that at least one amino acid residue in the BC loop is replaced by an amino acid sequence of interest;
       ii) a PCV2 ORF2 protein characterized in that an amino acid sequence of interest is inserted into the BC loop; or
       iii) a combination of i) and ii),
    b) an immunogenic composition containing the polypeptide of a),
    c) a polynucleotide comprising a sequence which encodes the polypeptide of a),
    d) a virus like particle composed of a plurality of the polypeptide of a),
    e) a baculovirus containing a polynucleotide comprising a sequence which encodes the polypeptide of a), and/or
    f) a plasmid and/or an expression vector, which comprises a polynucleotide comprising a sequence which encodes the polypeptide of a), and/or
for the preparation of a vaccine, wherein the amino acid sequence of interest comprises SEQ ID NO: 5 or 7.

23. A method for the treatment or prevention of an infection with PCV2, the reduction, prevention or treatment, of clinical signs caused by an infection with PCV2, or the prevention or treatment of a disease caused by an infection with PCV2a comprising administering the polypeptide of claim 1 and/or an immunogenic composition containing said polypeptide.

24. The method of claim 23 wherein the infection with PCV2 is an infection with PCV2 subtype b (PCV2b) and/or with PCV2 of a subtype other than subtype 2b.

25. The method of claim 23, wherein the infection with PCV2 is an infection with PCV2 of a subtype other than subtype 2b.

26. The method of claim 24, wherein the infection with PCV2 is a concurrent infection with (i) PCV2b and (ii) PCV2 of a subtype other than subtype 2b.

27. The method of claim 24, wherein the infection with PCV2 of a subtype other than subtype 2b is an infection with PCV2 subtype a (PCV2a) and/or PCV2 subtype c (PCV2c).

28. The method of claim 24, wherein the infection with PCV2 of a subtype other than subtype 2b is an infection with PCV2a.

29. The method of claim 23, wherein the infection with PCV2 is a concurrent infection with (i) PCV2b and (ii) PCV2a.

30. The method of claim 23, wherein said infection with PCV2b is an infection with a PCV2 comprising a polypeptide that is at least 94% identical to the sequence of SEQ ID NO:2 or comprising a polynucleotide which comprises a sequence encoding a polypeptide that is at least 94% identical to the sequence of SEQ ID NO:2.

31. The method of claim 23, wherein said infection with PCV2a is an infection with a PCV2 comprising a polypeptide that is at least 94% identical to the sequence of SEQ ID NO:3 or comprising a polynucleotide which comprises a sequence encoding a polypeptide that is at least 94% identical to the sequence of SEQ ID NO:3.

32. The method of claim 23, wherein the treatment or prevention of an infection with PCV2 comprises the induction of an immune response against said PCV2, wherein clinical signs of PCV2 infection are selected from the group consisting of lymphoid depletion, lymphoid inflammation, positive IHC for PCV2 antigen of lymphoid tissue, viremia, nasal shedding, pyrexia, reduced average daily weight gain, lung inflammation, positive IHC for PCV2 antigen of lung tissue, or said disease is PMWS.

33. The method of claim 32, wherein the treatment or prevention of an infection with PCV2 of a subtype other than 2b is based on or comprises or consists of the induction of an immune response against said PCV2 of a subtype other than 2b or the concurrent induction of an immune response against said PCV2 of a subtype other than 2b and PCV2b.

34. The method of claim 30, wherein said polypeptide and/or said immunogenic composition is administered only once.

35. A method of producing the polypeptide of claim 1, comprising transfecting a cell with a plasmid, an expression vector, and/or baculoviral vector comprising a polynucleotide sequence which encodes for the polypeptide of claim 1.

36. A method of determining whether an individual has received an immunogenic composition containing the polypeptide of claim 1, wherein said method comprises:
    a) obtaining a biological sample from an individual, and
    b) determining in the biological sample the presence or absence of one or more markers showing that the individual has received said amino acid sequence of interest,
wherein the presence of said one or more markers in said biological sample indicates that said individual has received said immunogenic composition.

37. The method of claim 36, wherein said one or more markers showing that the individual has received the amino acid sequence of interest are antibodies specific for said amino acid sequence of interest.

38. The method of claim 36, further comprising the steps of:
    a) contacting the biological sample with a capture reagent immobilized to a solid support, wherein the immobilized capture reagent is capable of binding said one or more markers, and
    b) determining the presence or absence of said one or more markers bound to the capture reagent, wherein the presence of said one or more markers bound to the capture reagent is indicative for the presence of said one or more markers in said biological sample.

39. The method of claim 36, wherein said method comprises determining in said biological sample the presence or absence of said one or more markers, wherein said markers are antibodies specific for said amino acid sequence of interest, and wherein said method comprises the steps of:
    a) contacting the biological sample with a capture reagent immobilized to a solid support, wherein the capture reagent is selected from the group consisting of:
        i) a protein comprising the amino acid sequence of interest,
        ii) a peptide comprising or consisting of the amino acid sequence of interest;
    b) separating the biological sample from the immobilized capture reagent;
    c) contacting the immobilized capture reagent-antibody complex with a detectable agent that binds to the antibody of the reagent-antibody complex; and
    d) measuring the level of antibody bound to the capture reagent using a detection means for the detectable agent.

40. The method of claim 39, wherein step d) further comprises a comparison with a standard curve to determine the level of antibody bound to the capture reagent.

41. The method of claim 39, wherein said detectable agent that binds to the antibody of the reagent-antibody complex is a detectable antibody and/or a labelled secondary antibody.

42. The method of claim 36, further comprising the step of determining in said biological sample the presence of one or more analytes selected from the group consisting of:
    i) antibodies specific for a polypeptide comprising or consisting of an amino acid sequence having at least 90% sequence identity with the amino acid sequence of SEQ ID NO:2, and
    ii) antibodies specific for a polypeptide comprising or consisting of an amino acid sequence having at least 90% sequence identity with the amino acid sequence of SEQ ID NO:3.

43. The method of claim 36, wherein the individual is a pig or a rabbit.

44. The method of claim 36, wherein the biological sample has been isolated from a pig.

45. The method of claim 36, wherein the biological sample is selected from the group consisting of whole blood, blood plasma, serum, urine, and oral fluids.

46. The method of claim 36, wherein the immobilized capture reagent is coated on a microtiter plate.

47. A kit for determining whether an individual has received an immunogenic composition containing the polypeptide of claim 1, wherein said kit contains one or more capture reagents immobilized to a solid support, wherein the one or more immobilized capture reagents are capable of binding antibodies specific for said amino acid sequence of interest.

48. The kit of claim 47, wherein the capture reagent is selected from the group consisting of:
- a) a protein or nucleic acid ligand comprising the amino acid sequence of interest; and
- b) a virus fragment or peptide comprising or consisting of the amino acid sequence of interest.

49. A recombinant polypeptide having at least 90% sequence identity with SEQ ID NO:1 selected from the group consisting of:
- a) a PCV2 ORF2 protein having at least 90% sequence identity with SEQ ID NO:2 characterized in that at least one amino acid residue in the BC loop is replaced by an amino acid sequence of interest;
- b) a PCV2 ORF2 protein having at least 90% sequence identity with SEQ ID NO:2 characterized in that an amino acid sequence of interest is inserted into the BC loop; or
- c) a combination of a) and b);

wherein the amino acid sequence of interest is an amino acid sequence consisting of 8 to 25 amino acid residues; and wherein the amino acid sequence of interest comprises SEQ ID NO: 5 or 7.

\* \* \* \* \*

```
                           SEQUENCE LISTING

<160> NUMBER OF SEQ ID NOS: 7

<210> SEQ ID NO 1
<211> LENGTH: 239
<212> TYPE: PRT
<213> ORGANISM: Artificial Sequence
<220> FEATURE:
<223> OTHER INFORMATION: corresponds to SEQ ID NO:2 with amino acid
      positions 58 to 64 being replaced by SEQ ID NO:6

<400> SEQUENCE: 1

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Glu Gln Lys Leu Ile Ser Glu
    50                  55                  60

Glu Asp Leu Thr Thr Pro Ser Trp Asn Val Asp Met Met Arg Phe Asn
65                  70                  75                  80

Ile Asn Asp Phe Leu Pro Pro Gly Gly Gly Ser Asn Pro Leu Thr Val
                85                  90                  95

Pro Phe Glu Tyr Tyr Arg Ile Arg Lys Val Lys Val Glu Phe Trp Pro
            100                 105                 110

Cys Ser Pro Ile Thr Gln Gly Asp Arg Gly Val Gly Ser Thr Ala Val
        115                 120                 125

Ile Leu Asp Asp Asn Phe Val Thr Lys Ala Asn Ala Leu Thr Tyr Asp
    130                 135                 140

Pro Tyr Val Asn Tyr Ser Ser Arg His Thr Ile Thr Gln Pro Phe Ser
145                 150                 155                 160

Tyr His Ser Arg Tyr Phe Thr Pro Lys Pro Val Leu Asp Arg Thr Ile
                165                 170                 175

Asp Tyr Phe Gln Pro Asn Asn Lys Arg Asn Gln Leu Trp Leu Arg Leu
            180                 185                 190

Gln Thr Thr Gly Asn Val Asp His Val Gly Leu Gly Thr Ala Phe Glu
        195                 200                 205

Asn Ser Ile Tyr Asp Gln Asp Tyr Asn Ile Arg Ile Thr Met Tyr Val
    210                 215                 220

Gln Phe Arg Glu Phe Asn Leu Lys Asp Pro Pro Leu Asn Pro Lys
225                 230                 235

<210> SEQ ID NO 2
<211> LENGTH: 234
<212> TYPE: PRT
<213> ORGANISM: Porcine circovirus

<400> SEQUENCE: 2
```

```
Met Thr Tyr Pro Arg Arg Phe Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Arg Thr
50                      55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
            85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
        130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
            165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
            195                 200                 205

Gln Asp Tyr Asn Ile Arg Ile Thr Met Tyr Val Gln Phe Arg Glu Phe
        210                 215                 220

Asn Leu Lys Asp Pro Pro Leu Asn Pro Lys
225                 230

<210> SEQ ID NO 3
<211> LENGTH: 233
<212> TYPE: PRT
<213> ORGANISM: Porcine circovirus

<400> SEQUENCE: 3

Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
50                      55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
            85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
        130                 135                 140
```

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 4
<211> LENGTH: 720
<212> TYPE: DNA
<213> ORGANISM: Artificial Sequence
<220> FEATURE:
<223> OTHER INFORMATION: encodes SEQ ID NO:1

<400> SEQUENCE: 4
atgacgtatc caaggaggcg tttccgcaga cgaagacacc gcccccgcag ccatcttggc      60
cagatcctcc gccgccgccc ctggctcgtc caccccgcc accgttaccg ctggagaagg      120
aaaaatggca tcttcaacac ccgcctctcc cgcaccatcg gttatactgt cgaacaaaag      180
ctcatctccg aggaagacct cacaacgccc tcctggaatg tggacatgat gagatttaat      240
attaatgatt tcttcccccc aggagggggc tcaaaccccc tcactgtgcc ctttgaatac      300
tacagaataa ggaaggttaa ggttgagttc tggccctgct ccccaatcac ccagggtgac      360
aggggagtgg gctccactgc tgttattcta gatgataact ttgtaacaaa ggccaatgcc      420
ctaacctatg acccctatgt aaactactcc tcccgccata ccataaccca gcccttctcc      480
taccactccc ggtactttac cccgaaacct gtccttgata ggacaatcga ttacttccaa      540
cccaataaca aaagaaatca actctggctg agactacaaa ctactggaaa tgtagaccat      600
gtaggcctcg gcactgcgtt cgaaaacagt atatacgacc aggactacaa tatccgtata      660
accatgtatg tacaattcag agaatttaat cttaagaccc cccacttaa ccctaagtga      720

<210> SEQ ID NO 5
<211> LENGTH: 11
<212> TYPE: PRT
<213> ORGANISM: Artificial Sequence
<220> FEATURE:
<223> OTHER INFORMATION: c-myc epitope

<400> SEQUENCE: 5

Glu Gln Lys Leu Ile Ser Glu Glu Asp Leu Thr
1               5                   10

<210> SEQ ID NO 6
<211> LENGTH: 16
<212> TYPE: PRT
<213> ORGANISM: Porcine reproductive and respiratory syndrome virus

<400> SEQUENCE: 6

Ser Ser His Leu Gln Leu Ile Tyr Asn Leu Thr Ile Cys Glu Leu Asn
1               5                   10                  15

<210> SEQ ID NO 7

```
<211> LENGTH: 11
<212> TYPE: PRT
<213> ORGANISM: Porcine reproductive and respiratory syndrome virus

<400> SEQUENCE: 7

Ser Ser His Leu Gln Leu Ile Tyr Asn Leu Thr
1               5                   10
```